US007141367B2

(12) United States Patent
Schwartz et al.

(10) Patent No.: US 7,141,367 B2
(45) Date of Patent: Nov. 28, 2006

(54) VARIANT TLR4 NUCLEIC ACID AND USES THEREOF

(75) Inventors: David A. Schwartz, Hillsborough, NC (US); Brian C. Schutte, Iowa City, IA (US); Eva Lorenz, Winston-Salem, NC (US)

(73) Assignee: University of Iowa Research Foundation, Iowa City, IA (US)

( * ) Notice: Subject to any disclaimer, the term of this patent is extended or adjusted under 35 U.S.C. 154(b) by 304 days.

(21) Appl. No.: 10/010,066

(22) Filed: Dec. 7, 2001

(65) Prior Publication Data

US 2002/0173001 A1 Nov. 21, 2002

Related U.S. Application Data

(63) Continuation of application No. PCT/US00/15723, filed on Jun. 8, 2000, which is a continuation-in-part of application No. 09/329,515, filed on Jun. 10, 1999, now Pat. No. 6,740,487.

(51) Int. Cl.
*C12Q 1/68* (2006.01)
*C12P 19/358* (2006.01)
*C07H 21/04* (2006.01)

(52) U.S. Cl. ........................ 435/6; 435/91.2; 536/24.3

(58) Field of Classification Search .................... 435/6, 435/91.2

See application file for complete search history.

(56) References Cited

FOREIGN PATENT DOCUMENTS

WO WO-98/50547 11/1998

OTHER PUBLICATIONS

Proc Natl Acad Sci U S A. Jan. 20, 1998;95(2):588-93. Rock FL, Hardiman G, Timans JC, Kastelein RA, Bazan JF. A family of human receptors structurally related to Drosophila Toll.*

Morris et al. A novel strategy for Directional Cloning of random primed cDNA. Innovations, No. 3, Jun. 1995 pp. 1-4.*

Arbour, N.C., et al., "Missense mutations of the TLR4 gene are associated with hyporesponsiveness to lipopolysaccharides (LPS) in humans", *Am. J. of Human Genetics*, vol. 65, No. 4, (Oct. 1999), p. A97.

Arbour, N.C., et al., "TLR4 mutations are associated with endotoxin hyporesponsivenss in humans", *Nature Genetics*, vol. 25, No. 2, (Jun. 2000), pp. 187-191.

Bonner, J.C., et al., "Induction of the Lung Myofibroblast PDGF Receptor System by Urban Ambient Particles From Mexico City", *American Journal of Respiratory Cell and Molecular Biology*, 19(4), (Oct. 1998), pp. 672-680.

Brigham, K.L., et al., "Endotoxin and Lung Injury", *American Review of Respiratory Disease*, (May 1986), pp. 913-927.

Chow, J.C., et al., "Toll-like Receptor-4 Mediates Lipopolysaccharide-induced Signal Transduction", *Journal of Biological Chemistry*, 274(16), (Apr. 1999),pp. 10689-10692.

Favorite, G.O., et al., "Effects Produced by the Intravenous Injection in Man of a Toxic Antigenic Material Derived From Eberthella Typhosa: Clinical Hematological, Chemical and Serological Studies", *Journal of Clinical Investigation*, (May 1942), pp. 589-599.

Hoshino, K., et al., "Cutting Edge: Toll-like Receptor 4 (TLR4)—Deficient Mice are Hyporesponsive to Lipopolysaccharide: Evidence for TLR4 as the Lps Gene Product", *Journal of Immunology*, 162(7), (1999), pp. 3749-3752.

Kuhns, D.B., et al., "Endotoxin and IL-1 Hyporesponsiveness in a Patient With Recurrent Bacterial Infections" , *Journal of Immunology*, 158(8), (Apr. 1997), pp. 3959-3964.

Medzhitov, R., et al., "A Human Homologue of the Drosophila Toll Protein Signals Activation of Adaptive Immunity", *Nature*, 388(6640), (1997), pp. 394-397.

Medzhitov, R..,et al. , "Innate Immunity: The Virtues of a Nonclonal System of Recognition", *Cell*, 91(3), (1997), pp. 295-298.

Michel, O., et al., "Effects of Inhaled Endotoxin on Bronchial Reactivity in Asthmatic and Normal Subjects", *Journal of Applied Physiology*, 66(3), (Mar. 1989), pp. 1059-1064.

Michel, O., et al., "Severity of Asthma is Related to Endotoxin in House Dust", *American Journal of Respiratory and Critical Care Medicine*, 154(6), (Dec. 1996), pp. 1641-1646.

Poltorak, A., et al., "Defective LPS Signaling in C3H/Hej and C57BL/10ScCr Mice: Mutations in Tlr4 Gene", *Science*, 282, (1998),pp. 2085-2088.

Qureshi, S.T., et al., "Endotoxin-tolerant Mice Have Mutations in Toll-like Receptor 4 (tlr4)", *Journal of Experimental Medicine*, 189(4), (1999), pp. 615-625.

Rock, F.L., et al., "A family of human receptors structurally related to Drosophila Toll", *Proc. Natl. Acad. Sci. USA*, vol. 95,(Jan. 1998), pp. 588-593.

Santamaria, P.,et al., "Invovlement of Class II MHC Molecules in the LPS-Induction of IL-1/TNF Secretions by Human Monocytes", *Journal of Immunology*, 143(3), (Aug. 1989), pp. 913-922.

Schwartz, D.A., et al., "Determinants of Longitudinal Changes in Spirometric Function Among Swine Confinement Operators and Farmers", *American Journal of Respiratory and Critical Care Medicine*, 151(1), (Jan. 1995), pp. 47-53.

Schwartz, D.A., et al., "The Role of Endotoxin in Grain Dust-induced Lung Disease", *American Journal of Respiratory and Critical Medicine*, 152(2), (Aug. 1995), pp. 603-608.

Wang, S..,et al. , "Effects of Inhalation of Steroids on Lung Permeability in Patients With Asthma", *Clinical Nuclear Medicine*, 20(6), (Jun. 1995), pp. 494-496.

Wright, S.D., et al., "CD14, a Receptor for Complexes of Lipopolysaccharide (LPS) and LPS Binding Protein", *Science*, 249(4975), (Sep. 1990), pp. 1431-1433.

Wright, S.D., "Toll, A New Prize in the Puzzle of Innate Immunity", *Journal of Experimental Medicine*, 189(4), (Feb. 1999), pp. 605-609.

Yang, R., et al., "Toll-like Receptor-2 Mediates Lipopolysaccharide-induced Cellular Signalling", *Nature*, 395(6699), (Sep. 1998), pp. 284-288.

* cited by examiner

*Primary Examiner*—Eileen B. O'Hara
*Assistant Examiner*—Fozia Hamud
(74) *Attorney, Agent, or Firm*—Schwegman, Lundberg, Woessner & Kluth, P.A.

(57) ABSTRACT

The invention provides methods to identify polymorphisms at the human TLR4 locus, as well as methods to identify individuals at risk of indications that increase their morbidity and mortality.

13 Claims, 23 Drawing Sheets

| Intron | Position | 5' to 3' sequence at EXON/intron boundary |
| --- | --- | --- |
| 1 | 135-136 | GCGTGGAGgtatgtggctggagtcagct ____ atttgtttgttttaaagACTTGGCC |
| 2 | 255-256 | TCACGGAGgttagaatgctgagcacgta ____ gtcatgtgtaatcattgcagGTGGTTCC |
| 3 | 422-423 | TTATCCAGgtaatgaatccactttaca ____ atgtcttttattcctgtagGTGTGAAA |

1 2 3 4

↓

| Human (aa 290) | . | . | . | L | A | Y | L | D | Y | Y | L | D | D | I | I | D | L | F | N | C | L | T | N | V | . | . | . |
|---|---|---|---|---|---|---|---|---|---|---|---|---|---|---|---|---|---|---|---|---|---|---|---|---|---|---|---|
| Mouse (aa 289) | . | . | . | L | T | Y | T | N | D | F | S | D | D | I | V | K | - | F | H | C | L | A | N | V | . | . | . |
| Rat (aa 289) | . | . | . | L | T | Y | I | N | H | F | S | D | D | I | Y | N | - | L | N | C | L | A | N | I | . | . | . |
| Hamster (aa 289) | . | . | . | F | T | Y | A | N | E | F | S | E | D | I | T | D | - | F | D | C | L | A | N | V | . | . | . |

FIG. 4

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 7

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 8

HUMAN TLR4 GENOMIC SEQUENCE

AAAATACTCC CTTGCCTCAA AAACTGCTCG GTCAAACGGT
GATAGCAAAC CACGCATTCA CAGGGCCACT GCTGCTCACA
AAACCAGTGA GGATGATGCC AGGATGATGT CTGCCTCGCG
CCTGGCTGGG ACTCTGATCC CAGCCATGGC CTTCCTCTCC
TGCGTGAGAC CAGAAAGCTG GGAGCCCTGC GTGGAGGTAT
GTGGCTGGAG TCAGCTCCTC TGAACTTTCC CTCACTTCTG
CCCAGAACTT CTCACTGTGT GCCCTGGTTT GTTTATTTTT
GCAAAAAAAA AAAGAGTTAA ATTACCTTAA AGACTCAAGA
AGCCACAGAG ATCAAATAAT TCATTGTTAC AGGGCACTAG
AGGCAGCCAT TGGGGGTTTG TTCCATTTGG AAATTTTGAG
TGCTAACAGG GGCATGAGAT AACATAGATC TGCTTAAGGT
CCCTGCTCTG CTACCTTGTG GCTCTGTGAA GAAATTATCA
AACCTGTCTG AGACTAGTTT TCGCATCTGT AAGAGAATTA
TAATACCTTC TTCACTAGAG AGTAAGCAGA CTGCTTCAGT
GTCATTTCTT CCCACTGGTG GTCTTTACAC TCAGCTTCAA
GCAGTCACCC TGCTCCTTTC AATCTCAGGA AAAAGATGGC
TTTGTGTGTG TGTCTCT:A: G:AGAAAGAA CTTTCTAAGT
TGGTGCAGA CTTCTGTATG CAGTAATATA GTTTAGTCCA
GAGGATGAAA AAAATAAGAG A:ATGAAAAA GGAAAAGAGA
GAGAGAGA:G AAGAAAAAAG CAAGAGGGAA AT:ATGTATA
ATGTCAGCTA ATGCAAC:AG TTTCTTTCTT AGTGAAATAC
CAATCAGCTG :GTTG:GTAA TCTT:ATTCA TGATGGATCT
CTTTTGTTTT TCCCCTGCGC AGACTTC:AC AGTTGCTTTA
GAAACCCATA GTAGAGCCGA A:CAGCTAAG AAAATGATTT
ACAGTGAGGC AGGGTCAGAA ACTCAAGAGA GAAAAAGCCA
GCTGCAGTC: CTGAAGT:TG AGGATATAGG :AGAAAATCA
AGTAATATTT AGCAAAGACT AATTCATTAT CTTGAAGCCA
TCCCTTCCCT CAATTCCCTG CCCATAGTCC TCCTCCTTGT
CCTCTTCTCT GNA:TCCCTC TGCTGTTAGG TTA:ATGG:A
GATAGATTTT CTAATTANGC TCACTGCGAG ATAAAACCCA
GCCCATGTTT CTATTAGNCA ATATTGTCTT TGAGGCTCCA
TGGCTTGCAN CATTTAAGCA GACATACGAA TGAAGATCTG
CATGTTTGAA CTCTGACTTT GCGCATATTA CTTCATTTCT
TTGAATTTCC ATTTTCCTCA TCTTTAAATG CTTATTTGAA
GATTAAGTGA AAGTATATAA CAAACAAGAA CTATGCAGGC
GTATGGTAAG GGATTAATGA TAGATGATAA TAATTAATGT
TGACATCTAT TGATCACTTA TACTGTAGCG GGCTTTTAAA
TAAACTCTTT AAACACCTTA TCTCATTTAA TCCTTCAAAC
ATTCTATTGG TTTCAAACAA CAGAAAACTA CAATTAGCTG
GCTTCTGCAA GGAATTTTGT TGGAGGAAAT GAGAGCATTC
AGAAATTAGA TGGGAGCGTT AGAGAATTAG GCTTACAAAG
AATGTGGGAA AGTAGGCTAG AAAGCAGTGT AAAAACAAAG
ACAGCATAAA GCACTTGACC TTATTTACTA GGTTCCACCA
TGGGAATCCA TGCACTCTAA AGATTTCCCC CTATTTCTAC
ATCACTTTGC TCAAGGGTCA ATGAGCCAAG GAAAAGAATG

FIG. 9A

```
CAGTTGTCAA AATCTGGGCC ATGACTAAGG AAGGTCTGGA
CATCTTGACT GCCAGACAGT CTCCCCAATG ATATGGAGTA
TTTAGAATGA TACTGGATAT TTTATTTATT TTTTGTATTT
TCAACTTTTA AGTTCAGAGG CACATGTGCA GAGCATGCAG
GTTTATTACA TAAGTAAATG TGTGCCATGG TGATTTGCTG
CATAGATCAT GAAAATATGG AACGCATCAT GGATTTGTGT
GTCATCCTTG TGCAGGGGCC ATGCTCATCT TCTCTGTATC
CTTCCAATTT TAGTATATGT GCTACTGCAG CAAGCACGAT
ATTGGATATT TTATTACCTA CATTTTACAT ATGATAAAAT
GAGGCTCACT GAGGTTTTTC TTTTGTTCGT TTTATTTTGT
TTTGTTTTTA AAGACTTGGC CCTAAACCAC ACAGAAGAGC
TGGCATGAAA CCCAGAGCTT TCAGACTCCG GAGCCTCAGC
CCTTCACCCC GATTCCATTG CTTCTTGCTA AATGCTGCCG
TTTTATCNCG GAGGTTAGAA TGCTGAGCAC GTAGTAGGTG
CTCTTTACTT TCTAATCTAG AGTAAGACAA TTTATAAGCA
TGAATTGAGT GAATGGATGG ATGGATATAT GGATGGAAGG
ATGGACAGAT GGATGAAAGG TTGACTGAAT TTTGTGCTTG
CACAAAAAGA GGCCCCTCTC CACCATCTCT GGTCTAGGAG
AGGGGAGTTG GGAGACCATG CAGTAAAGAT ACTTCATGTC
ATGTGTAATC ATTGCAGGTG GTTCCTAATA TTACTTATCA
ATGCATGGAG CTGAATTTCT ACAAAATCCC CGACAACCTC
CCCTTCTCAA CCAAGAACCT GGACCTGAGC TTTAATCCCC
TGAGGCATTT AGGCAGCTAT AGCTTCTTCA GTTTCCCAGA
ACTGCAGGTG CTGGATTTAT CCAGGTAATG AATCCACTTT
TACATACTGC ACAAGGTGAG GTGTTCATTG TCCTATCATT
TCATTATTGG ACTGGAAAGC TTGGTTTGTG GAGTCTCATC
TTCATTCACT TATTCATTCA TACAACAGAT GTCTTATTAA
CTATATAACC TTGAGCAAGC TACCTCTATT CTCCAGGTCT
CAGTTTTCTA ATCTGTGAAG TAGGCAGTTG GCTGAGACAG
CTTCTAAGGG CAATTCTAAT TTTAGGTTTT CTTTTAAGAC
AGGAGAGAAA ATTAGCTTAA ATTCTTTCAT AAGCAGCTAT
TTATTGACTA CTTGCTATAT GTTGTACACT CTGCAAGAAG
ACAGGCATAT ATTGATATAT AACACACAGC CCCTGTTGTT
AAGGAGGCAT ATCTTCTTGA AAGAGTTAAT ACCTTAAAGT
CCTGGGTATG GTCCTGGGTA CATAGTATAT AGTCAACACA
TTTTAATTAT GATTTTTTGG ATCTGGAAAC TGATATAAAG
ATAGCGACAT ATAACAGTAG GTGATAAATT ATGTTTAAAC
TAAAGGTAAC TAATTGTATT TTTCAGAAGA GGGGCCTTCT
CTGTGGTGGG TAGTCAAGAA AGATTCATGA ACTGCATAAG
ATTCAAACAA TGTCTAGAAT ATTAAAACTA GTGGTGGCAG
GTGAAATGTC ATCTTGATAT TTTAGGGGAA CCAAATTCTA
AAAGGGTTTT CATCATCGGG GCCTTATTTG CAAATCGAAC
TAGATAATGG ATCATGTTCT CTGCAATGGT TTGTAAAACA
TTTCAAAACA TTTTACATAT TTTTTATTAT AGAAATTATT
GATAAAGACT AAGGTCACAG TATAAAAATC CTTTTTAGAG
CAGACATTTC TGTAGAAGAG TGAACATATG ACCTATTATA
CTCTAATTTG GATATAGATA GGATGTAACA AAGGAGTAAT
```

FIG. 9A (Continued)

```
GGGAACAATT CAAAGGCAGT GGTATAGTGC ATANAGTCCT
GTTGGGGTCA GAAGACCTGA GCCCAAGTTT ACCCCCAACA
TTTATAACCC ATGTAACCTT AGCATATTAC TTCATCTCCC
TTAATCCTTA GTTTCATATC TGATCAATGG AAATGATGAA
ACTTATTCTG CTGGATTAAA TGTGATAATA AATATTAATA
TGCTGTATAT ATTTAAATTT TTATAAAATA TATTTATAA
GCATAAAGTA TTCTTACAGA ATTTCATTAG GTTTTTAAAA
TAATTTCAAC TTTTATTTTT GATTCAGGGA TTTACATGGT
TATATTGCGT AATGCTGAGG TGTAGGGTAC AATCGATACC
ATCACTCAGG TAGTGAGCAT AGTACCCAAT AGTTAGTTTT
TCAACCCTTG CTGCTTTCTC TCTATCCCCT CTCTAGTAAT
CCCCAGGGTC TATTTTTGTC ATCTTTATGT CCATGTGTAC
TCCATGTTTG GATCCTACTT ATAAAGTGAG AACTCATGGT
ATTTGGCTTT CTGTNCCTTT GTTNGCTAAT TTGCTTAGGA
TAATGGCTAC TAGCTGCATC TATGCCATTA TGTTCTAAAT
TTCANTTNCC TGCATGAAAA TTTTGTCAAG TACTCTATTA
AGGTAGACCA CCTCTCCCTT TTTTTTTCAA ACAAGAAGTA
GNTTTTCCCA AACAATGCCC TTATGGAATT NATCTTCAAT
CCNNGGATAC CCAATAACTT GCCCCAAANC CTTAATCTGN
CTTACAGAGA GGCCACCTTC CTTCTGTAAC CCATAGGAGA
TTTGGATTGG TAAGAATGCT TTGTGATAGC CCAGCAGCCT
TCTTTCCCCT ATAGAAATAT ATATATANTC TTTTTATAGG
TGAGGAACTG AAGCTTGAAT AATTTAAATG ACTTATATAC
ATNATCATTG CTTGTTAGCC ACAGACCAGA GATTTAAGTT
CNCATCTCCA GAATCCAACT TAAATGTTTT CTTTGTCTTA
ATACTCTACT TCTCTAAAGT GATTATCACC AATGTAATGA
TATAGAGNCA CAGCAAGACC CTTTCCTTCT CACCTAATGT
ATAGAGCAAT GCAGAGATAG AATGATGGGC TATAACAATC
ATATAATTGA AAGAAAGAAC TTCAAAAATA ATCAAGTTCA
GCTGTTTGAT TTATAAATGT GATAACTAAA ACCTAGAGAG
GAAAAGAGGT ACTCAAGATC ACACAGTAGG AGAGGACTGC
AGAAACACCA AACCCAAGCT CTTTTGTCCA CTCTTCCAGC
GTTCTTTCTA CTATACTGCC TATCCTTTAT CTAGTTACCA
ATAAATAACA AAAGCTTGGA CCACAATGCT TTTATTGTCT
AGGAAACTCC TGAAGAAGCT AAATAAAATG GGTGGGGAAT
ATTGTAAATG TAATTCAGGC TGGATTAAGA AAGAACTTAT
TTGACATTGT AACTGACAAG CACCTGCAAT GCTGAAAGGA
ATTTTTCATT GGCNTGCTGT TTGCTGGGCT GCATCAAAGC
CCTGTCTCTA GGACATGTCT CTGAACATTG TGTGTAGCAT
GGCTTTCATT TCTTTTAGGA TAAAATTCAA AACCCTTTAT
CTGGTTGGTA AACCTCTGCC TAATTGGGAA CCTTCTTTCT
CCACAACTCC ATATTGTACA CTCCAATTTC ATCTCTGTTC
TCCAACCATG GAAGCTATTT GTCATGATTC CTCCTTGTGT
CATTTTTTTT CTGTCAACCT TGGGGCTTTT GTGTTTGCTG
TTCACTTCAC CTCCTTTTAT TGTTAACTTC TACTCATCTT
TCAATTTTCA ACTTAAGTGT TCTCAGAGAA ACCTACTTTG
ATTTTCTTGG TCCANAACGG TTCTCTGGAT GTGAACTCTT
```

FIG. 9A (Continued)

```
ATAGCACATA ATTTTCACTT TTTTCCACAA AACTCGCTCC
TATCACCTGT TACAAGCATT TACCTCTGAT AACAAGAACT
TTCAAATATC TAGCTGTCAT GTAAGCACTT TTCATAAACA
TTAAGAGTAT CTGTGACACT TATGTGTAAT GTTTCGTATC
TCTGAAATTG ATATTTACCA GTCATTTATC TTGGCTACCA
ACTAACAACT ATCCATATTA TCTGTACCAA TCAGATGTAT
AATCACAATT TTGTGTGACA GAAAATGGCT AAACTTGATC
CAAGGCTATT ACATGCTTT: ATCAACTGCA CAATCTTTAT
ATATGTCAAT TATTGATCTT TAACTGATTT CCTTCTTATG
:GATTTTCTC CTCTGCTTAT CATGTATGCC TAACAT:GAC
AAAAAAG:AG CCTA:TCATT GCAGCCAGTA TGATAATACT
CA:GTCTGTG GGGCTTCTTA TTTGCTTAT: TCCATCATCA
TCTGTCCTGC TTGATGTCTT TGCCTATGCA CAATCATATG
:ACCCATCAC ATCTGTATGA AGAGC:TGGA TGACTAGGAT
TAATATTCT: AT:::TTTAG GTTCTTATT: CAGCAGAAAT
ATTAGATAA: TCAATGTCTT TTTATTCCTG TAGGTGTGAA
ATCCAGACAA TTGAAGATGG GGCATATCAG AGCCT:AAGC
CACCTCTCTA CCTTAATATT GACAGGAAAC CCCATCCAGA
GTTTAGCCCT GGGAGCCTTT TCTGGACTAT CAAGTTTACA
GAAGCTGGTG GCTGTGGAGA CAAATCTAGC ATCTCTAGAG
AACTTCCCCA TTGGACATCT CAAAACTTTG AAAGAACTTA
ATGTGGCTCA CAATCTTATC CAATCTTTCA AATTACCTGA
GTATTTTTCT AATCTGACCA ATCTAGAGCA CTTGGACCTT
TCCAGCAACA AGATTCAAAG TATTTATTGC ACAGACTTGC
GGGTTCTACA TCAAATGCCC CTACTCAATC TCTCTTTAGA
CCTGTCCCTG AACCCTATGA ACTTTATCCA ACCAGGTGCA
TTTAAAGAAA TTAGGCTTCA TAAGCTGACT TTAAGAAATA
ATTTTGATAG TTTAAATGTA ATGAAAACTT GTATTCAAGG
TCTGGCTGGT TTAGAAGTCC ATCGTTTGGT TCTGGGAGAA
TTTAGAAATG AAGGAAACTT GGAAAAGTTT GACAAATCTG
CTCTAGAGGG CCTGTGCAAT TTGACCATTG AAGAATTCCC
GATTAGCATA CTTAGACTAC TACCTCGATG ATATTATTGA
CTTATTTAAT TGGTTGACAA ATGGTTCTTC ATTTTCCCTG
GTGAGTGTGA CTATTGAAAG GGTAAAAGAC TTTTCTTATA
ATTTCGGATG GCAACATTTA GAATTAGTTA ACTGTAAATT
TGGACAGTTT CCCACATTGA AACTCAAATC TCTCAAAAGG
CTTACTTTCA CTTCCAACAA AGGTGGGAAT GCTTTTTCAG
AAGTTGATCT ACCAAGCCTT GAGTTTCTAG ATCTCAGTAG
AAATGGCTTG AGTTTCAAAG GTTGCTGTTC TCAAAGTGAT
TTTGGGACAA CCA:GCCT:A AAGTATTTAG ATCTGAGCTT
CAATGGTGTT A:TTACCATG AGTTCAAACT TCTTGGGCTT
AGAACA:ACT AGAACATCTG GATTTCCAGC ATTCCAATTT
GAAACA:AAT GAGTGAGTTT TCAGTATTCC TA:TCACTCA
GAAA:CCT:C ATTTACCTTG ACATTTCTCA TACTCACACC
AGAGTTGCTT TCAATGGCAT CTTCAATGGC TTGTCCAGTC
TCGAAGTCTT GAAAATGGCT GGCAATTCTT TCCAGGAAAA
CTTCCTTCCA GATATCTTCA CAGAGCTGAG AAACTTGACC
```

FIG. 9A (Continued)

```
TTCCTGGACC TCTCTCAGTG TCAACTGGAG CAGTTGTCTC
CAACAGCATT TAACTCACTC TCCAGTCTTC AGGTACTAAA
TATGAGCCAC AACAACTTCT TTTCATTGGA TACGTTTCCT
TATAAGTGTC TGAACTCCCT CCAGGTTCTT GATTACAGTC
TCAATCACAT AATGACTTCC AAAAAACAGG AACTACAGCA
TTTTCCAAGT AGTCTAGCTT TCTTAAATCT TACTCAGAAT
GACTTTGCTT GTACTTGTGA ACACCAGAGT TTCCTGCAAT
GGATCAAGGA CCAGAGGCAG CTCTTGGTGG AAGTTGAACG
AATGGAATGT GCAACACCTT CAGATAAGCA GGGCATGCCT
GTGCTGAGTT TGAATATCAC CTGTCAGATG AATAAGACCA
TCATTGGTGT GTCGGTCCTC AGTGTGCTTG TAGTATCTGT
TGTAGCAGTT CTGGTCTATA AGTTCTATTT TCACCTGATG
CTTCTTGCTG GCTGCATAAA GTATGGTAGA GGTGAAAACA
TCTATGATGC CTTTGTTATC TACTCAAGCC AGGATGAGGA
CTGGGTAAGG AATGAGCTAG TAAAGAATTT AGAAGAAGGG
GTGCCTCCAT TTCAGCTCTG CCTTCACTAC AGAGACTTTA
TTCCCGGTGT GGCCATTGCT GCCAACATCA TCCATGAAGG
TTTCCATAAA AGCCGAAAGG TGATTGTTGT GGTGTCCCAG
CACTTCATCC AGAGCCGCTG GTGTATCTTT GAATATGAGA
TTGCTCAGAC CTGGCAGTTT CTGAGCAGTC GTGCTGGTAT
CATCTTCATT GTCCTGCAGA AGGTGGAGAA GACCCTGCTC
AGGCAGCAGG TGGAGCTGTA CCGCCTTCTC AGCAGGAACA
CTTACCTGGA GTGGGAGGAC AGTGTCCTGG GGCGGCACAT
CTTCTGGAGA CGACTCAGAA AAGCCCTGCT GGATGGTAAA
TCATGGAATC CAGAAGGAAC AGTGGGTACA GGATGCAATT
GGCAGGAAGC AACATCTATC TGAAGAGGAA AAATAAAAAC
CTCCTGAGGC ATTTCTTGCC CAGCTGGGTC CAACACTTGT
TCAGTTAATA AGTATTAAAT GCTGCCACAT GTCAGGCCTT
ATGCTAAGGG TGAGTAATTC CATGGTGCAC TAGATATGCA
GGGCTGCTAA TCTCAAGGAG CTTCCAGTGC AGAGGGAATA
AATGCTAGAC TAAAATACAG AGTCTTCCAG GTGGGCATTT
CAACCAACTC AGTCAAGGAA CCCATGACAA AGAAAGTCAT
TTCAACTCTT ACCTCATCAA GTTGAATAAA GACAGAGAAA
ACAGAAAGAG ACATTGTTCT TTTCCTGAGT CTTTTGAATG
GAAATTGTAT TATGTTATAG CCATCATAAA ACCATTTTGG
TAGTTTTGAC TGAACTGGGT GTTCACTTTT TCCTTTTTGA
TTGAATACAA TTTAAATTCT ACTTGATGAC TGCAGTCGTC
AAGGGGCTCC TGATGCAAGA TGCCCCTTCC ATTTTAAGTC
TGTCTCCTTA CAGAGGTTAA AGTCTAGTGG CTAATTCCTA
AGGAAACCTG ATTAACACAT GCTCACAACC ATCCTGGTCA
TTCTCGAGCA TGTTCTATTT TTTAACTAAT CACCCCTGAT
ATATTTTTAT TTTTATATAT CCAGTTTTCA TTTTTTTACG
TCTTGCCTAT AAGCTAATAT CATAAATAAG GTTGTTTAAG
ACGTGCTTCA AATATCCATA TTAACCACTA TTTTTCAAGG
AAGTATGGAA AAGTACACTC TGTCACTTTG TCACTCGATG
TCATTCCAAA GTTATTGCCT ACTAAGTAAT GACTGTCATG
AAAGCAGCAT TGAAATAATT TGTTTAAAGG GGGCACTCTT
```

FIG. 9A (Continued)

TTAAACGGGA AGAAAATTTC CGCTTCCTGG TCTTATCATG
GACAATTTGG GCTATAGGCA TGAAGGAAGT GGGATTACCT
CAGGAAGTCA CCTTTTCTTG ATTCCAGAAA CATATGGGCT
GATAAACCCG GGGTGACCTC ATGAAATGAG TTGCAGCAGA
TGTTTATTTT TTTCAGAACA AGTGATGTTT GATGGACCTA
TGAATCTATT TAGGGAGACA CAGATGGCTG GGATCCCTCC
CCTGTACCCT TCTCACTGCC AGGAGAACTA CGTGTGAAGG
TATTCAAGGC AGGGAGTATA CATTGCTGTT TCCTGTTGGG
CAATGCTCCT TGACCACATT TTGGGAAGAG TGGATGTTAT
CATTGAGAAA ACAATGTGTC TGGAATTAAT GGGGTTCTTA
TAAAGAAGGT TCCCAGAAAA GAATGTTCAT TCCAGCTTCT
TCAGGAAACA GGAACATTCA AGGAAAAGGA CAATCAGGAT
GTCATCAGGG AAATGAAAAT AAAAACCACA ATGAGATATC
ACCTTATACC AGGTAGATGG CTACTATAAA AAAATGAAGT
GTCATCAAGG ATATAGAGAA ATTGGAACCC TTCTTCACTG
CTGGAGGGAA TGGAAAATGG TGTAGCCGTT ATGAAAAACA
GTACGGAGGT TTCTCAAAAA TTAAAAATAG AACTGCTATA
TGATCCAGCA ATCTCACTTC TGTATATATA CCCAAAATAA
TTGAAATCAG AATTTCAAGA AAATATTTAC ACTCCCATGT
TCATTGTGGC ACTCTTCACA ATCACTGTTT CCAAAGTTAT
GGAAACAACC CAAATTTCCA TTGGAAAATA AATGGACAAA
GGAAATGTGC ATATAACGTA CAATGGGGAT ATTATTCAGC
CTAAAAAAAG GGGGGATCCT GTTATTTATG ACAACATGAA
TAAACCCGGA GGCCATTATG CTATGTAAAA TGAGCAAGTA
ACAGAAAGAC AAATACTGCC TGATTTCATT TATATGAGGT
TCTAAAATAG TCAAACTCAT AGAAGCAGAG AATAGAACAG
TGGTTCCTAG GGAAAAGGAG GAAGGGAGAA ATGAGGAAAT
AGGGAGTTGT CTAATTGGTA TAAAATTATA GTATGCAAGA
TGAATTAGCT CTAAAGATCA GCTGTATAGC AGAGTTCGTA
TAATGAACAA TACTGTATTA TGCACTTAAC ATTTTGTTAA
GAGGGTACCT CTCATGTTAA GTGTTCTTAC CATATACATA
TACACAAGGA AGCTTTTGGA GGTGATGGAT ATATTTATTA
CCTTGATTGT GGTGATGGTT TGACAGGTAT GTGACTATGT
CTAAACTCAT CAAATTGTAT ACATTAAATA TATGCAGTTT
TATAATATCA AAAAAAAAAA AAAAAAAA

FIG. 9A (Continued)

```
   1  TTCCACTTCT AAGAGCTGCC TAGAGTAGTC AAGATTATAG AGACAAAAGT
  51  AGTGCATAGA TTCAAGGGCC TAGGGAAAGG GGAAATGGGG AGTTATTTAT
 101  TAATGAATAG TGGTGATGAT TGTACAAAAA TATGAACATA ATTAATGCCA
 151  CTAAATTGTN CACATACAAA TGGTCAAGAT AATAAATTTT ATGTTATGTC
 201  ATGTTATGTT ATGTGATTTT ACCATAATAC AGAAAATGAA AAAAGAAAAG
 251  AAAGAAAGTA AAGCTTAGCG GTTTNCATGA CTTGNCCAAT GCCTCAAAGC
 301  CATGAGTCGA CCCAGCTGAG ATCTGANCTT CAGTATATTC CATTCTGAAA
 351  TCCCAGACTT TTCCCAATCT TCTTGTACTT TTCAAACTGT GTTTCAGTTG
 401  AGGTTTATTT TCAGTTTTGT ATGTGAGTTT CTTCGCAAGA AGGGCGGGCC
 451  AAATTGTGTC CTGCAAAAAC CTACATATCG AAGTCCTAAC CCCTCTACCT
 501  CAGACTATGA CTGTATATGG AGAGAGAGCC TTGAAAGAGG TATGTAAGGT
 551  AGAATGAGGT CATTATGGTG GGCCCTAATC CAACATAACT GGTGTCCTTA
 601  TAAGAAGGGG AGATTAGAAT TCAGACACAC TTGCTGACAC CTTGAGTTCA
 651  GACTGGAAGC CTCTAGAATT GTGAGAAAAT GAATGTCTGT TGTTTAAGCC
 701  ACCCAGTCTG TGGTATTTCC TTATGGCAGC CCCAGCAAAC TAATACAAAT
 751  AGTGTTTCCA CAGCTGAAAC AAAATTGGAA AATCACCGTC ATCCTAGAGA
 801  GTTACAAGGG CTATTTTAAT AGAACCTGAT TGTTTTCCTA AATTCACCAA
 851  GCCCAGGCAG AGGTCAGATG ACTAATTGGG ATAAAAGCCA ACTAGCTTCC
 901  TCTTGCTGTT TCTTTAGCCA CTGGTCTGCA GGCGTTTTCT TCTTCTAACT
 951  TCCTCTCCTG TGACAAAAGA GATAACTATT AGAGAAACAA AAGTCCAGAA
1001  TGCTAAGGTT GCCGCTTTCA CTTCCTCTCA CCCTTTAGCC CAGAACTGCT
1051  TTGAATACAC CAATTGCTGT GGGGCGGCTC GAGGAAGAGA AGACACCAGT
1101  GCCTCAGAAA CTGCTCGGTC AGACGGTGAT AGCGAGCCAC GCATTCACAG
1151  GGCCACTGCT GCTCACAGAA GCAGTGAGGA TGATGCCAGG ATGATGTCTG
1201  CCTCGCGCCT GGCTGGGACT CTGATCCCAG CCATGGCCTT CCTCTCCTGC
1251  GTGAGACCAG AAAGCTGGGA GCCCTGCGTG GAGGTATGTG GCTGGAGTCA
1301  GCTCCTCTGA ACTTTCCCTC ACTTCTGCCC AGAACTTCTC ACTGTGTGCC
1351  CTGGTTTGTT
```

FIG. 9B

```
   1 CGCATCATGG ATTTGTGTGT CATCCTTGTG CAGGGGCCAT GCTCATCTTC
  51 TCTGTATCCT TCCAATTTTA GTATATGTGC TACTGCAGCA AGCACGATAT
 101 TGGATATTTT ATTACCTACA TTTTACATAT GATAAAATGA GGCTCACTGA
 151 GGTTTTTCTT TTGTTCGTTT TATTTTGTTT TGTTTTTAAA GACTTGGCCC
 201 TAAACCACAC AGAAGAGCTG GCATGAAACC CAGAGCTTTC AGACTCCGGA
 251 GCCTCAGCCC TTCACCCCGA TTCCATTGCT TCTTGCTAAA TGCTGCCGTT
 301 TTATCACGGA GGTTAGAATG CTGAGCACGT AGTAGGTGCT CTTTACTTTC
 351 TAATCTAGAG TAAGACAATT TATAAGCATG AATTGAGTGA ATGGATGGAT
 401 GGATATATGG ATGGAAGGAT GGACAGATGG ATGAAAGGTT GACTGAATTT
 451 TGTGCTTGCA CAAAAAGAGG CCCCTCTCCA CCATCTCTGG TCTAGGAGAG
 501 GGGAGTTGGG AGACCATGCA GTAAAGATAC TTCATGTCAT GTGTAATCAT
 551 TGCAGGTGGT TCCTAATATT ACTTATCAAT GCATGGAGCT GAATTTCTAC
 601 AAAATCCCCG ACAACCTCCC CTTCTCAACC AAGAACCTGG ACCTGAGCTT
 651 TAATCCCCTG AGGCATTTAG GCAGCTATAG CTTCTTCAGT TTCCCAGAAC
 701 TGCAGGTGCT GGATTTATCC AGGTAATGAA TCCACTTTTA CATACTGCAC
 751 AAGGTGAGGT GTTCATTGTC CTATCATTTC ATTATTGGAC TGGAAAGCTT
 801 GGTTTGTGGA GTCTCATCTT CATTCACTTA TTCATTCATA CAACAGATGT
 851 CTTATTAACT ATATAACCTT GAGCAAGCTA CCTCTATTCT CCAGGTCTCA
 901 GTTTTCTAAT CTGTGAAGTA GGCAGTTGGC TGAGACAGCT TCTAAGGGCA
 951 ATTCTAATTT TAGGTTTTCT TTTAAGACAG GAGAGAAAAT TAGCTTAAAT
1001 TCTTTCATAA GCAGCTATTT ATTGACTACT TGCTATATGT TGTACACTCT
1051 GCAAGAAGAC AGGCATATAT TGATATATAA CACACAGCCC CTGTTGTTAA
1101 GGAGGCATAT CTTCTTGAAA GAGTTAATAC CTTAAAGTCC TGGGTATGGT
1151 CCTGGGTACA TAGTATATAG TCAACACATT TTAATTATGA TTTTTTGGAT
1201 CTGGAAACTG ATATAAAGAT AGCGACATAT AACAGTAGGT GATAAATTAT
1251 GTTTAAACTA AAGGTAACTA ATTGTATTTT TCAGAAGAGG GGCCTTCTCT
1301 GTGGTGGGTA GTCAAGAAAG ATTCATGAAC TGC
```

FIG. 9C

```
   1 GGTAAGAATG CTTTGTGATA GCCCAGCAGC CTTCTTTCCC CTATAGAAAT
  51 ATATATATAN TCTTTTTATA GGTGAGGAAC TGAAGCTTGA ATAATTTAAA
 101 TGACTTATAT ACATNATCAT TGCTTGTTAG CCACAGACCA GAGATTTAAG
 151 TTCNCATCTC CAGAATCCAA CTTAAATGTT TTCTTTGTCT TAATACTCTA
 201 CTTCTCTAAA GTGATTATCA CCAATGTAAT GATATAGAGN CACAGCAAGA
 251 CCCTTTCCTT CTCACCTAAT GTATAGAGCA ATGCAGAGAT AGAATGATGG
 301 GCTATAACAA TCATATAATT GAAAGAAAGA ACTTCAAAAA TAATCAAGTT
 351 CAGCTGTTTG ATTTATAAAT GTGATAACTA AAACCTAGAG AGGAAAAGAG
 401 GTACTCAAGA TCACACAGTA GGAGAGGACT GCAGAAACAC CAAACCCAAG
 451 CTCTTTTGTC CACTCTTCCA GCGTTCTTTC TACTATACTG CCTATCCTTT
 501 ATCTAGTTAC CAATAAATAA CAAAAGCTTG GACCACAATG CTTTTATTGT
 551 CTAGGAAACT CCTGAAGAAG CTAAATAAAA TGGGTGGGGA ATATTGTAAA
 601 TGTAATTCAG GCTGGATTAA GAAAGAACTT ATTTGACATT GTAACTGACA
 651 AGCACCTGCA ATGCTGAAAG GAATTTTTCA TTGGCNTGCT GTTTGCTGGG
 701 CTGCATCAAA GCCCTGTCTC TAGGACATGT CTCTGAACAT TGTGTGTAGC
 751 ATGGCTTTCA TTTCTTTTAG GATAAAATTC AAAACCCTTT ATCTGGTTGG
 801 TAAACCTCTG CCTAATTGGG AACCTTCTTT CTCCACAACT CCATATTGTA
 851 CACTCCAATT TCATCTCTGT TCTCCAACCA TGGAAGCTAT TTGTCATGAT
 901 TCCTCCTTGT GTCATTTTTT TTCTGTCAAC CTTGGGGCTT TTGTGTTTGC
 951 TGTTCACTTC ACCTCCTTTT ATTGTTAACT TCTACTCATC TTTCAATTTT
1001 CAACTTAAGT GTTCTCAGAG AAACCTACTT TGATTTTCTT GGTCCANAAC
1051 GGTTCTCTGG ATGTGAACTC TTATAGCACA TAATTTTCAC TTTTTTCCAC
1101 AAAACTCGCT CCTATCACCT GTTACAAGCA TTTACCTCTG ATAACAAGAA
1151 CTTTCAAATA TCTAGCTGTC ATGTAAGCAC TTTTCATAAA CATTAAGAGT
1201 ATCTGTGACA CTTATGTGTA ATGTTTCGTA TCTCTGAAAT TGATATTTAC
1251 CAGTCATTTA TCTTGGCTAC CAACTAACAA CTATCCATAT TATCTGTACC
1301 AATCAGATGT ATAATCACAA TTTTGTGTGA CAGAAAATGG CTAAACTTGA
1351 TCCAAGGCTA TTACATGCTT TATCAACTGC ACAATCTTTA TATATGTCAA
1401 TTATTGATCT TTANCTGATT TCCTTCTTAT GGATTTTCTC CTCTGCTTAT
1451 CATGTATGCC TAACATGACA AAAAAGAGCC TATCATTGCA GCCAGTATGA
1501 TAATACTCAG TCTGTGGGGC TTCTTATTTG CTTATTCCAT CATCATCTGT
1551 CCTGCTTGAT GTCTTTGCCT ATGCACAATC ATATGACCCA TCACATCTGT
1601 ATGAAGAGCT GGATGACTAG GATTAATATT CTATTTTAGG TTCTTATTCA
1651 GCAGAAATAT TAGATAATCA ATGTCTTTTT ATTCCTGTAG GTGTGAAATC
1701 CAGACAATTG AAGATGGGGC ATATCAGAGC CTAAGCCACC TCTCTACCTT
1751 AATATTGACA GGAAACCCCA TCCAGAGTTT AGCCCTGGGA GCCTTTTCTG
1801 GACTATCAAG TTTACAGAAG CTGGTGGCTG TGGAGACAAA TCTAGCATCT
1851 CTAGAGAACT TCCCCATTGG ACATCTCAAA ACTTTGAAAG AACTTAATGT
1901 GGCTCACAAT CTTATCCAAT CTTTCAAATT ACCTGAGTAT TTTTCTAATC
1951 TGACCAATCT AGAGCACTTG GACCTTTCCA GCAACAAGAT TCAAAGTATT
2001 TATTGCACAG ACTTGCGGGT TCTACATCAA ATGCCCCTAC TCAATCTCTC
2051 TTTAGACCTG TCCCTGAACC CTATGAACTT TATCCAACCA GGTGCATTTA
2101 AAGAAATTAG GCTTCATAAG CTGACTTTAA GAAATAATTT TGATAGTTTA
2151 AATGTAATGA AAACTTGTAT TCAAGGTCTG GCTGGTTTAG AAGTCCATCG
2201 TTTGGTTCTG GGAGAATTTA GAAATGAAGG AAACTTGGAA AAGTTTGACA
```

FIG. 9D

2251 AATCTGCTCT AGAGGGCCTG TGCAATTTGA CCATTGAAGA ATTCCGATTA
2301 GCATACTTAG ACTACTACCT CGATGATATT ATTGACTTAT TTAATTGTTT
2351 GACAAATGTT TCTTCATTTT CCCTGGTGAG TGTGACTATT GAAAGGGTAA
2401 AAGACTTTTC TTATAATTTC GGATGGCAAC ATTTAGAATT AGTTAACTGT
2451 AAATTTGGAC AGTTTCCCAC ATTGAAACTC AAATCTCTCA AAAGGCTTAC
2501 TTTCACTTCC AACAAAGGTG GGAATGCTTT TTCAGAAGTT GATCTACCAA
2551 GCCTTGAGTT TCTAGATCTC AGTAGAAATG GCTTGAGTTT CAAAGGTTGC
2601 TGTTCTCAAA GTGATTTTGG GACAACCAGC CTAAAGTATT TAGATCTGAG
2651 CTTCAATGGT GTTATTACCA TGAGTTCAAA CTTCTTGGGC TTAGAACAAC
2701 TAGAACATCT GGATTTCCAG CATTCCAATT TGAAACAAAT GAGTGAGTTT
2751 TCAGTATTCC TATCACTCAG AAACCTCATT TACCTTGACA TTTCTCATAC
2801 TCACACCAGA GTTGCTTTCA ATGGCATCTT CAATGGCTTG TCCAGTCTCG
2851 AAGTCTTGAA AATGGCTGGC AATTCTTTCC AGGAAAACTT CCTTCCAGAT
2901 ATCTTCACAG AGCTGAGAAA CTTGACCTTC CTGGACCTCT CTCAGTGTCA
2951 ACTGGAGCAG TTGTCTCCAA CAGCATTTAA CTCACTCTCC AGTCTTCAGG
3001 TACTAAATAT GAGCCACAAC AACTTCTTTT CATTGGATAC GTTTCCTTAT
3051 AAGTGTCTGA ACTCCCTCCA GGTTCTTGAT TACAGTCTCA ATCACATAAT
3101 GACTTCCAAA AAACAGGAAC TACAGCATTT TCCAAGTAGT CTAGCTTTCT
3151 TAAATCTTAC TCAGAATGAC TTTGCTTGTA CTTGTGAACA CCAGAGTTTC
3201 CTGCAATGGA TCAAGGACCA GAGGCAGCTC TTGGTGGAAG TTGAACGAAT
3251 GGAATGTGCA ACACCTTCAG ATAAGCAGGG CATGCCTGTG CTGAGTTTGA
3301 ATATCACCTG TCAGATGAAT AAGACCATCA TTGGTGTGTC GGTCCTCAGT
3351 GTGCTTGTAG TATCTGTTGT AGCAGTTCTG GTCTATAAGT TCTATTTTCA
3401 CCTGATGCTT CTTGCTGGCT GCATAAAGTA TGGTAGAGGT GAAAACATCT
3451 ATGATGCCTT TGTTATCTAC TCAAGCCAGG ATGAGGACTG GGTAAGGAAT
3501 GAGCTAGTAA AGAATTTAGA AGAAGGGGTG CCTCCATTTC AGCTCTGCCT
3551 TCACTACAGA GACTTTATTC CCGGTGTGGC CATTGCTGCC AACATCATCC
3601 ATGAAGGTTT CCATAAAAGC CGAAAGGTGA TTGTTGTGGT GTCCCAGCAC
3651 TTCATCCAGA GCCGCTGGTG TATCTTTGAA TATGAGATTG CTCAGACCTG
3701 GCAGTTTCTG AGCAGTCGTG CTGGTATCAT CTTCATTGTC CTGCAGAAGG
3751 TGGAGAAGAC CCTGCTCAGG CAGCAGGTGG AGCTGTACCG CCTTCTCAGC
3801 AGGAACACTT ACCTGGAGTG GGAGGACAGT GTCCTGGGGC GGCACATCTT
3851 CTGGAGACGA CTCAGAAAAG CCCTGCTGGA TGGTAAATCA TGGAATCCAG
3901 AAGGAACAGT GGGTACAGGA TGCAATTGGC AGGAAGCAAC ATCTATCTGA
3951 AGAGGAAAAA TAAAAACCTC CTGAGGCATT TCTTGCCCAG CTGGGTCCAA
4001 CACTTGTTCA GTTAATAAGT ATTAAATGCT GCCACATGTC AGGCCTTATG
4051 CTAAGGGTGA GTAATTCCAT GGTGCACTAG ATATGCAGGG CTGCTAATCT
4101 CAAGGAGCTT CCAGTGCAGA GGGAATAAAT GCTAGACTAA AATACAGAGT
4151 CTTCCAGGTG GGCATTTCAA CCAACTCAGT CAAGGAACCC ATGACAAAGA
4201 AAGTCATTTC AACTCTTACC TCATCAAGTT GAATAAAGAC AGAGAAAACA
4251 GAAAGAGACA TTGTTCTTTT CCTGAGTCTT TTGAATGGAA•ATTGTATTAT
4301 GTTATAGCCA TCATAAAACC ATTTTGGTAG TTTTGACTGA ACTGGGTGTT
4351 CACTTTTTCC TTTTTGATTG AATACAATTT AAATTCTACT TGATGACTGC
4401 AGTCGTCAAG GGGCTCCTGA TGCAAGATGC CCCTTCCATT TTAAGTCTGT
4451 CTCCTTACAG AGGTTAAAGT CTAGTGGCTA ATTCCTAAGG AAACCTGATT
4501 AACACATGCT CACAACCATC CTGGTCATTC TCGAGCATGT TCTATTTTTT
4551 AACTAATCAC CCCTGATATA TTTTTATTTT TATATATCCA GTTTTCATTT

FIG. 9D (Continued)

```
4601  TTTTACGTCT TGCCTATAAG CTAATATCAT AAATAAGGTT GTTTAAGACG
4651  TGCTTCAAAT ATCCATATTA ACCACTATTT TTCAAGGAAG TATGGAAAAG
4701  TACACTCTGT CACTTTGTCA CTCGATGTCA TTCCAAAGTT ATTGCCTACT
4751  AAGTAATGAC TGTCATGAAA GCAGCATTGA AATAATTTGT TTAAAGGGGG
4801  CACTCTTTTA AACGGGAAGA AAATTTCCGC TTCCTGGTCT TATCATGGAC
4851  AATTTGGGCT AGAGGCAGGA AGGAAGTGGG ATGACCTCAG GAGGTCACCT
4901  TTTCTTGATT CCAGAAACAT ATGGGCTGAT AAACCCGGGG TGACCTCATG
4951  AAATGAGTTG CAGCAGAAGT TTATTTTTTT CAGAACAAGT GATGTTTGAT
5001  GGACCTCTGA ATCTCTTTAG GGAGACACAG ATGGCTGGGA TCCCTCCCCT
5051  GTACCCTTCT CACTGCCAGG AGAACTACGT GTGAAGGTAT TCAAGGCAGG
5101  GAGTATACAT TGCTGTTTCC TGTTGGGCAA TGCTCCTTGA CCACATTTTG
5151  GGAAGAGTGG ATGTTATCAT TGAGAAAACA ATGTGTCTGG AATTAATGGG
5201  GTTCTTATAA AGAAGGTTCC CAGAAAAGAA TGTTCATCCA GCCTCCTCAG
5251  AAACAGAACA TTCAAGAAAA GGACAATCAG GATGTCATCA GGGAAATGAA
5301  AATAAAAACC ACAATGAGAT ATCACCTTAT ACCAGGTAGA ATGGCTACTA
5351  TAAAAAAATG AAGTGTCATC AAGGATATAG AGAAATTGGA ACCCTTCTTC
5401  ACTGCTGGAG GGAATGGAAA ATGGTGTAGC CGTTATGAAA AACAGTACGG
5451  AGGTTTCTCA AAAATTAAAA ATAGAACTGC TATATGATCC AGCAATCTCA
5501  CTTCTGTATA TATACCCAAA ATAATTGAAA TCAGAATTTC AAGAAAATAT
5551  TTACACTCCC ATGTTCATTG TGGCACTCTT CACAATCACT GTTTCCAAAG
5601  TTATGGAAAC AACCCAAATT TCCATTGAAA AATAAATGGA CAAAGAAAAT
5651  GTGCATATAC GTACAATGGG ATATTATTCA GCCTAAAAAA AGGGGGNATC
5701  CTGTTATTTA TGACAACATG AATAAACCCG GAGCCATTAT GCTATGTAAA
5751  ATGAGCAAGT AACAGAAAGA CAAATACTGC CTGATTTCAT TTATATGAGG
5801  TTCTAAAATA GTCAAACTCA TAGAAGCAGA GAATAGAACA GTGGTTCCTA
5851  GGGAAAAGGA GGAAGGGAGA AATGAGGAAA TAGGGAGTTG TCTAATTGGT
5901  ATAAAATTAT AGTATGCAAG ATGAATTAGC TCTAAAGATC AGCTGTATAG
5951  CAGAGTTCGT ATAATGAACA ATACTGTATT ATGCACTTAA CATTTTGTTA
6001  AGAGGGTACC TCTCATGTTA AGTGTTCTTA CCATATACAT ATACACAAGG
6051  AAGCTTTTGG AGGTGATGGA TATATTTATT ACCTTGATTG TGGTGATGGT
6101  TTGACAGGTA TGTGACTATG TCTAAACTCA TCAAATTGTA TACATTAAAT
6151  ATATGCAGTT TTATAATATC AATTATGTCT GAATGAAGCT ATAAAAAAGA
6201  AAAGACAACA AAATTCAGTT GTCAAAACTG GAAATATGAC CACAGTCAGA
6251  AGTGTTTGTT ACTGAGTGTT TCAGAGTGTG TTTGGTTTGA GCAGGTCTAG
6301  GGTGATTGAA CATCCCTGGG TGTGTTTCCA TGTCTCATGT ACTAGTGAAA
6351  GTAGATGTGT GCATTTGTGC ACATATCCCT ATGTATCCCT ATCAGGGCTG
6401  TGTGTATTTG AAAGTGTGTG TGTCCGCATG ATCATATCTG TATAGAAGAG
6451  AGTGTGATTA TATTTCTTGA AGAATACATC CATTTGAAAT GGATGTCTAT
6501  GGCTGTTTGA GATGAGTTCT CTACTCTTGT GCTTGTACAG TAGTCTCCCC
6551  TTATCCCTTA TGCTTGGTGG ATACGTTCTT AGACCCCAAG TGGATCTCTG
6601  AGACCGCAGA TGGTACCAAA CCTCATATAT GCAATATTTT TTCCTATACA
6651  TAAATACCTA AGATAAAGTT CATCTTCTGA ATTAGGCACA GTAAGAGATT
6701  AACAATAACT AACAATAAAA TTGAATAGTT ATAATAATAT ATTGTAATAA
6751  AAGTTATGTG AATGTGATCT CTTTCTTTTC TCTCTC
```

FIG. 9D (Continued)

VARIANT TLR4 NUCLEIC ACID AND USES THEREOF

RELATED APPLICATIONS

This application is a continuation under 35 USC 111(a) of International Application Serial No. PCT/US00/15723 filed on Jun. 8, 2000 and published in English on Dec. 21, 2000 as WO 00/77204 A1, which is a continuation-in-part of U.S. application Ser. No. 09/329,515, filed Jun. 10, 1999; now U.S. Pat. No. 6,740,487, which applications are incorporated herein by reference.

STATEMENT OF GOVERNMENT RIGHTS

This invention was made at least in part with a grant from the Government of the United States of America (grants ES06537, ES07498 and ES05605 from the National Institute of Environmental Sciences, grant HL62628 from the National Heart and Lung Institute, and grant RR00059 from the General Clinical Research Centers Program). The Government may have certain rights in the invention.

BACKGROUND OF THE INVENTION

Endotoxin or lipopolysaccharide (LPS), released from the cell wall of bacteria, plays a central role in a broad spectrum of human disease. The pathogenic importance of LPS in gram-negative sepsis is well established. Intravenous LPS induces all of the clinical features of gram-negative sepsis, including fever, shock, leukopenia followed by leukocytosis, and disseminated intravascular coagulation (Favorite et al., 1942). Higher concentrations of circulating levels of endotoxin have been associated with manifestations of systemic inflammatory response syndrome (Wang et al., 1995) and the development of acute respiratory distress syndrome following sepsis (Brigham et al., 1986). Inhaled endotoxin can induce airflow obstruction in naive or previously unexposed subjects (Michel et al., 1992) and is the most important occupational exposure associated with the development Schwartz et al., 1995a), and progression (Schwartz et al., 1995b), of airway disease among exposed workers. The concentration of endotoxin in the domestic setting appears to be associated with the clinical severity of asthma (Michel et al., 1996). Moreover, recent studies have shown that endotoxin is a contaminant of particulate matter in air pollution and may play a role in the pathophysiologic consequences of air pollution (Bonner et al., 1998). Thus, endotoxin is an important cause of morbidity and mortality.

The ability of the host to respond to endotoxin may play an important role in determining the severity of the physiologic and biologic response to this frequently encountered toxin. In mice, genetic differences in susceptibility to LPS have been established. LPS hyporesponsiveness arose spontaneously and was first identified in the C3H/HeJ strain. This strain had an $LD_{50}$ for LPS at least 20 times that observed in A/HeJ mice (Sultzer et al., 1968). In addition to C3H/HeJ, two other mouse strains, C57BL/10ScCR (Coutinho et al., 1978) and its progenitor strain, C57BL/10ScN, (Vogel et al., 1979), are hyporesponsive to LPS.

Moreover, several reports suggest that humans may also respond differently to LPS. A patient with recurrent bacterial infections has been reported to be refractory to the in vivo and in vitro effects of LPS (Kuhns et al., 1997). Following challenge with intravenous LPS, this patient had no systemic increase in IL-6 or G-CSF and had a minimal rise in the concentration of leukocytes, TNF-α, and IL-8. Inter-individual differences have also been reported in the release and synthesis of cytokines by monocytes stimulated with LPS in vitro (Santamaria et al., 1989).

LPS is thought to cause much of its morbidity and mortality by activating kinases (DeFranco et al., 1998) that control the function of transcription factors (nuclear factor-κB and AP-1) and ultimately lead to production of pro-inflammatory cytokines and co-stimulatory molecules (Wright, 1999). Several lines of evidence suggest that the toll receptor (TLR) family, and specifically TLR4 and TLR2 regulate the interaction between LPS and intracellular kinases and may serve as a proximal target to interrupt LPS signaling (Wright, 1998; Medzhitov et al., 1997). Both TLR4 and TLR2 activate signaling through NF-κB and AP-1 in transfected human cell lines (Medzhitov et al., 1997; Yang et al., 1998), and TLR4 mediates LPS induced signal transduction (Chow et al., 1999). CD14, a glycosylphosphatidyl inositol-linked receptor that binds LPS (Poltorak et al., 1998a) enhances LPS induced TLR2 (Yanget al., 1998) and TLR4 (Chow et al., 1998) signaling, suggesting that the toll receptors interact with CD14 to initiate the cellular response to LPS. Studies in mice indicate that 1) the TLR4 gene maps to the critical region in LPS hyporesponsive mice (Poltorak et al., 1998), 2) mutations in the TLR4 gene (Poltorak et al., 1998; Qureshi et al., 1999) are found in mouse strains (C3H/HeJ and C57BL10/ScCr) that are defective in their response to LPS, and 3) disruption of the TLR4 gene results in a LPS hyporesponsive phenotype (Hoshino et al., 1999).

Thus, there is need to determine whether the human TLR4 gene is polymorphic, and whether any particular polymorphism is associated with disease, e.g., LPS hyporesponsiveness.

SUMMARY OF THE INVENTION

The invention provides a method to identify a mammal, e.g., a human, at risk of, or having, an indication associated with altered innate immunity, e.g., to bacterial infection. The method comprises contacting an amount of DNA obtained from a human physiological sample with an amount of at least one TLR4-specific oligonucleotide under conditions effective to amplify the DNA so as to yield amplified DNA. Then it is determined whether the amplified DNA comprises a nucleotide substitution, e.g., one that results in an amino acid substitution, i.e., the TLR4 DNA of the human encodes a variant TLR4. Thus, the invention is useful to detect polymorphisms in the TLR4 gene.

Normal healthy, non-asthmatic subjects demonstrate a reproducible airway response to an incremental LPS inhalation challenge test, with some subjects developing airflow obstruction when challenged with low concentrations of LPS and others virtually unaffected by high concentrations of inhaled LPS. These findings suggest that the spectrum of LPS responsiveness in humans is quite variable from one individual to the next (but reproducible within an individual), and that a substantial portion of the population may be hyporesponsive to inhaled LPS. As described hereinbelow, an incremental LPS inhalation challenge test was employed to reliably phenotype individuals as either responsive (at least a 20% decline in the forced expiratory volume in one second ($FEV_1$) after inhaling up to 41.5 μg LPS) or hyporesponsive ($FEV_1$>80% of their baseline after inhaling 41.5 μg of LPS) to inhaled LPS. Fifty-two (63%) of these individuals were responsive to inhaled LPS and 31 (37%) were hyporesponsive to inhaled LPS.

These results were employed to determine the relationship between polymorphisms in the TLR4 gene and the airway response to inhaled LPS in the 83 normal healthy, non-asthmatic subjects. Using single stranded conformational variant (SSCV) analysis and direct sequencing, a missense mutation (A896G) was identified in the fourth exon of the TLR4 gene that results in replacement of a conserved aspartic acid residue with glycine at position 299 in the extracellular domain of the TLR4 receptor. The Asp299Gly sequence variant occurred in 3 LPS responsive (5.8%) and 7 LPS hyporesponsive (22.6%) study subjects (p=0.03). Among the subjects with the common TLR4 allele (N=73), the dose-response slope (percent decline $FEV_1$/cumulative dose of inhaled LPS) averaged a 1.86% decline in $FEV_1$/μg inhaled LPS (range 0.01%–19.78%), while the dose-response slope for the subjects with the Asp299Gly allele (N=10) was significantly less (p=0.007), averaging 0.59% decline in $FEV_1$/μg inhaled LPS (range 0.00%–1.59%). Thus, a sequence polymorphism in the TLR4 gene, i.e., a missense mutation (Asp299Gly) in the fourth exon of the TLR4 gene, occurs in a substantial portion of the population, and is associated with an airway hyporesponsive in humans challenged with inhaled LPS. The allelic frequency of the A896G substitution was 6.6% in the study population, 7.9% in a normal control population from Iowa (Lidral et al., 1998), and 3.3% in the parental chromosomes of the CEPH population (NIH-CEPH, 1992). As also described herein, the presence of a TLR4 mutation was associated with gram negative sepsis, severity of sepsis, pre-term delivery, and respiratory distress syndrome in pre-term infants.

The invention also provides an isolated and purified nucleic acid molecule comprising a nucleic acid segment, e.g., genomic DNA or cDNA, encoding TLR4, such as a variant TLR4. Also provided are primers, oligonucleotides and probes comprising the isolated nucleic acid sequences of the invention. The nucleic acid molecules of the invention may be single stranded or double stranded.

Transfection of CHO cells with either the wild-type or the mutant (Asp299Gly) allele of the TLR4 gene demonstrated that this mutation interrupts TLR4-mediated LPS signaling. Moreover, the wild-type allele of TLR4 rescues the LPS hyporesponsive phenotype in either airway epithelial cells or alveolar macrophages obtained from individuals with the TLR4 mutation. Thus, these results provide the first genetic evidence that a common mutation causes differences in LPS responsiveness that may contribute to several disease states in humans.

Therefore, the invention further provides an expression cassette comprising a nucleic acid molecule of the invention, a host cell transformed with the expression cassette, and TLR4 polypeptides isolated therefrom. The transformed host cells, or isolated TLR4 polypeptides, may be useful in identifying agents that modulate, i.e., enhance or inhibit, TLR4 activity. For example, an expression cassette comprising a nucleic acid molecule of the invention which encodes a variant TLR4 polypeptide is introduced to murine cells, e.g., oocytes via microinjection (see Sigmund et al., 1993). The resulting pups are screened for the presence of the nucleic acid molecule. Hence, the invention also provides a transgenic mouse, the genome of the cells of which is augmented with variant human TLR4 DNA. Human TLR4 transgenic mice of the invention have altered innate immunity, e.g., they are more susceptible to gram negative sepsis than their nontransgenic counterparts.

The invention also provides a method to treat an individual at risk of, or having, an indication associated with altered innate immunity, in which an agent that alters TLR4 activity is administered to the individual.

BRIEF DESCRIPTION OF THE FIGURES

FIG. 4. The aspartic acid residue at position 299 is conserved. A portion of the predicted amino acid sequence is aligned for the TLR4 genes from human (Rock et al., 1998; SEQ ID NO:4), mouse (Poitorak et al., 1998; SEQ ID NO:5), rat (Genbank Accession No. AF057025; SEQ ID NO:6), and hamster (D. Golenbock, SEQ ID NO:7). The position of the first amino acid in each sequence is given. The aspartic acid at position 299 is indicated with an arrow. Conserved amino acids are shaded.

FIG. 7. Codons.

FIG. 8. Exemplary amino acid substitutions.

FIG. 9. A) A partial nucleotide sequence of genomic human TLR4 DNA (SEQ ID NO:62). B) The 5' UTR, exon 1 (nt 1100–1283), and a partial sequence of intron 1 (Genbank Accession No. AF172169; SEQ ID NO:70). C) Exon 2 (nt 192–311), exon 3 (nt 556–722), and intron 2 (244 bp) (Genbank Accession No. AF172170; SEQ ID NO:71). D) Exon 4 (nt 1691–6172) and the 3' UTR (Genbank Accession No. AF172171; SEQ ID NO:72).

DETAILED DESCRIPTION OF THE INVENTION

Figure 1:
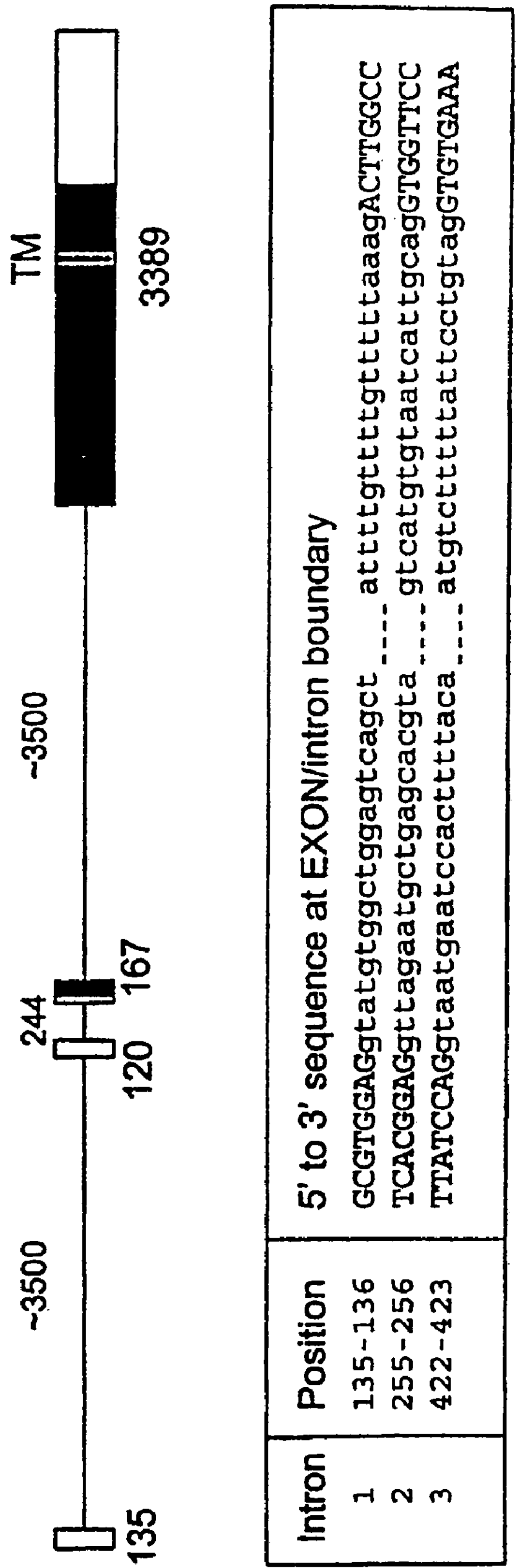
FIG. 1. Genomic structure for the human TLR4 gene (exons are represented by boxes and introns are represented by lines). The coding sequence is in black and the nucleotides encoding the transmembrane domain (TM) are shaded. The positions of the introns in the published TLR4 cDNA sequence (Rock et al., 1998; Genbank Accession No. U88880) are listed. The exon (caps) and intron (lower case) sequences at each of the splice junctions is shown (sequences at 5' and 3' splice junctions for intron 1, SEQ ID NO:1 and SEQ ID NO:63, respectively; for intron 2, SEQ ID NO:2 and SEQ ID NO:64, respectively; and for intron 3, SEQ ID NO:3 and SEQ ID NO:65, respectively).

As used herein, the terms "isolated and/or purified" refer to in vitro preparation, isolation and/or purification of a nucleic acid molecule or polypeptide, so that it is not associated with in vivo substances. Thus, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. An isolated nucleic acid molecule means a polymeric form of nucleotides of at least 10 bases in length, either ribonucleotides or deoxynucleotides or a modified form of either type of nucleotide. The term includes single and double stranded forms of DNA. The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for primers or probes; although oligonucleotides may be double stranded, e.g., for use in the construction of a variant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phophoroselenoate, phosphorodiselenoate, phosphoroanilothioate, phosphoraniladate, phosphoroamidate, and the like. An oligonucleotide can include a label for detection, if desired.

The term "isolated polypeptide" means a polypeptide encoded by genomic DNA, cDNA or recombinant RNA, or is synthetic origin, or some combination thereof, which isolated polypeptide (1) is not associated with proteins found in nature, (2) is free of other proteins from the same source, e.g., free of human proteins, (3) is expressed by a cell from a different species, or (4) does not occur in nature.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of sequence from one TLR4 allele that is compared to another TLR4 allele. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with preferably increasing homologies of at least about 70%, about 90%, about 95%, about 98%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp. 1–10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (*U.S.A.*) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

An isolated "variant" TLR4 polypeptide has at least 50%, preferably at least about 80%, and more preferably at least about 90%, but less than 100%, contiguous amino acid sequence homology or identity to the amino acid sequence of a reference (wild-type) TLR4 polypeptide. Preferably, the TLR4 polypeptides of the invention are biologically active. Biologically active polypeptides include those that induce an immune response when administered to an organism, are bound by antibodies specific for TLR4, activate signaling through NF-kB and AP-1, interact with CD14, or induce cytokine release following LPS stimulation. While it is preferred that a variant TLR4 has at least about 0.1%, preferably at least about 1%, and more preferably at least about 10%, of the activity of wild-type TLR4, the invention includes variant TLR4 polypeptides having no detectable biological activity. Likewise, a "variant" TLR4 nucleic acid molecule has at least about 80%, preferably at least about 90% and more preferably at least about 95%, but less than 100% contiguous nucleic acid sequence homology or identity to the nucleic acid sequence of a wild-type TLR4 gene.

As used herein, an "indication or condition associated with aberrant, modified or altered innate immunity" includes, but is not limited to, hyporesponsiveness to LPS, susceptibility to infection with gram-negative bacteria, susceptibility to sepsis by gram-negative bacteria, susceptibility to chronic airway disease, susceptibility to asthma, susceptibility to arthritis, susceptibility to pyelonephritis, susceptibility to gall bladder disease, susceptibility to pneumonia, susceptibility to bronchitis, susceptibility to chronic obstructive pulmonary disease, severity of cystic fibrosis, and susceptibility to local and systemic inflammatory conditions, e.g., systemic inflammatory response syndrome (SIRS), local gram negative bacterial infection, or acute respiratory distress syndrome (ARDS).

A. Nucleic Acid Molecules of the Invention

1. Sources of the Nucleic Acid Molecules of the Invention

Sources of nucleotide sequences from which the present nucleic acid molecules encoding TLR4, a portion (fragment) thereof, a variant thereof or the nucleic acid complement thereof, include total or polyA$^{+}$ RNA from any mammalian, preferably human, cellular source from which cDNAs can be derived by methods known in the art. Other sources of the DNA molecules of the invention include genomic libraries derived from any mammalian cellular source. Moreover, the present DNA molecules may be prepared in vitro, e.g., by synthesizing an oligonucleotide of about 100, preferably about 75, more preferably about 50, and even more preferably about 40, nucleotides in length, or by subcloning a portion of a DNA segment that encodes a particular TLR4.

2. Isolation of a Gene Encoding TLR4

A nucleic acid molecule encoding TLR4 can be identified and isolated using standard methods, as described by Sambrook et al., *Molecular Cloning: A Laboratory Manual*, Cold Spring Harbor, N.Y. (1989). For example, reverse-transcriptase PCR (RT-PCR) can be employed to isolate and clone TLR4 cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.,* 51, 263 (1987); Erlich, ed., *PCR Technology*, (Stockton Press, NY, 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other mammalian TLR4. One primer is prepared which is predicted to anneal to the antisense strand, and another primer prepared which is predicted to anneal to the sense strand, of a DNA molecule which encodes TLR4.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs which encode TLR4 is to screen a cDNA or genomic library. Screening for DNA fragments that encode all or a portion of a DNA encoding TLR4 can be accomplished by probing the library with a probe which has sequences that are highly conserved between genes believed to be related to TLR4, e.g., the homolog of a particular TLR4 from a different species, or by screening of plaques for binding to antibodies that specifically recognize TLR4. DNA fragments that bind to a probe having sequences which are related to TLR4, or which are immunoreactive with antibodies to TLR4, can be subcloned into a suitable vector and sequenced and/or used as probes to identify other cDNAs encoding all or a portion of TLR4.

Thus, "isolated and/or purified TLR4" nucleic acid refers to in vitro isolation of a nucleic acid molecule from its natural cellular environment, and from association with other components of the cell, such as nucleic acid or polypeptide, so that it can be sequenced, replicated, and/or expressed. For example, "isolated TLR4 nucleic acid" is RNA or DNA containing greater than 9, preferably 36, and more preferably 45 or more, sequential nucleotide bases that encode at least a portion of TLR4, a variant thereof, RNA or DNA complementary thereto, or which hybridizes to, RNA or DNA comprising TLR4 sequences, and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

As used herein, the term "recombinant nucleic acid", e.g., "recombinant DNA sequence or segment", refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.,* 9, 6103 (1981), and Goeddel et al., *Nucleic Acids Res.,* 8, 4057 (1980). Therefore, "isolated DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

3. Variants of the Nucleic Acid Molecules of the Invention

Nucleic acid molecules encoding amino acid sequence variants of TLR4 are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of TLR4 nucleic acid.

Oligonucleotide-mediated mutagenesis is a preferred method for preparing amino acid substitution variants of TLR4. This technique is well known in the art as described by Adelman et al., *DNA,* 2, 183 (1983). Briefly, TLR4 DNA is altered by hybridizing an oligonucleotide encoding the desired mutation to a DNA template, where the template is the single-stranded form of a plasmid or bacteriophage containing the unaltered or native DNA sequence of TLR4. After hybridization, a DNA polymerase is used to synthesize an entire second complementary strand of the template that will thus incorporate the oligonucleotide primer, and will code for the selected alteration in the TLR4 DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.,* 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.,* 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of TLR4, and the other strand (the original template) encodes the native, unaltered sequence of TLR4. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-($\alpha$S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

For example, a preferred embodiment of the invention is an isolated and purified DNA molecule comprising a human DNA segment encoding a variant TLR4 having a nucleotide substitution at position 896 (A896G) which encodes an amino acid substitution (Asp299Gly). Other nucleotide substitutions which result in silent mutations, missense mutations, or a nonsense mutations, can be ascertained by reference to FIG. 7, FIG. 8 and page D1 in Appendix D in Sambrook et al., *Molecular Cloning: A Laboratory Manual* (1989).

B. Chimeric Expression Cassettes

To prepare expression cassettes for transformation herein, the recombinant DNA sequence or segment may be circular or linear, double-stranded or single-stranded. A DNA sequence which encodes an RNA sequence that is substantially complementary to a mRNA sequence encoding TLR4 is typically a "sense" DNA sequence cloned into a cassette in the opposite orientation (i.e., 3' to 5' rather than 5' to 3'). Generally, the DNA sequence or segment is in the form of chimeric DNA, such as plasmid DNA, that can also contain coding regions flanked by control sequences which promote the expression of the DNA present in the resultant cell line.

As used herein, "chimeric" means that a vector comprises DNA from at least two different species, or comprises DNA from the same species, which is linked or associated in a manner which does not occur in the "native" or wild type of the species.

Aside from DNA sequences that serve as transcription units for TLR4, or portions thereof, a portion of the recombinant DNA may be untranscribed, serving a regulatory or a structural function. For example, the DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase luc gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

C. Transformation into Host Cells

The recombinant DNA can be readily introduced into the host cells, e.g., mammalian, bacterial, yeast or insect cells by transfection with an expression vector comprising DNA encoding TLR4 or its complement, by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. Viral vectors, useful to introduce genes to mammalian cells include, but are not limited to, poxvirus vectors, herpes simplex virus I vectors, adenovirus vectors, adeno-associated virus vectors, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence.

To confirm the presence of the DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular TLR4, e.g., by immunological means (ELISAs and Western blots) or by assays described herein.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

D. TLR4 Polypeptides, Variants, and Derivatives thereof

The present isolated, purified TLR4 polypeptides, variants or derivatives thereof, can be synthesized in vitro, e.g., by the solid phase peptide synthetic method or by recombinant DNA approaches (see above). The solid phase peptide synthetic method is an established and widely used method, which is described in the following references: Stewart et al., *Solid Phase Peptide Synthesis*, W. H. Freeman Co., San Francisco (1969); Merrifield, *J. Am. Chem. Soc.* 85 2149 (1963); Meienhofer in "Hormonal Proteins and Peptides," ed.; C. H. Li, Vol. 2 (Academic Press, 1973), pp. 48–267; Bavaay and Merrifield, "The Peptides," eds. E. Gross and F. Meienhofer, Vol. 2 (Academic Press, 1980) pp. 3–285; and Clark-Lewis et al., *Meth. Enzymol.,* 287, 233 (1997). These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given TLR4 can be readily prepared. For example, amides of the TLR4 or TLR4 variants of the present invention may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide or peptide variant of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the TLR4 or variant thereof may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the peptide or peptide variant. Other amino-terminal modifications include aminooxypentane modifications (see Simmons et al., *Science,* 276, 276 (1997)).

In addition, the amino acid sequence of TLR4 can be modified so as to result in a variant TLR4. The modification includes the substitution of at least one amino acid residue in the polypeptide for another amino acid residue, including substitutions which utilize the D rather than L form, as well as other well known amino acid analogs, e.g., unnatural amino acids such as α, α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, stating, 1,2,3,4,-tetrahydroisoquinoline-3-carboxylic acid, penicillamine, ornithine, citrulline, α-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, (ω-N-methylarginine, and other similar amino acids and imino acids and tert-butylglycine.

Conservative amino acid substitutions include aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying the activity of the polypeptide variant. Such assays are described herein.

Conservative substitutions are shown in FIG. 8 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic; trp, tyr, phe.

The invention also envisions polypeptide variants with non-conservative substitutions. Non-conservative substitutions entail exchanging a member of one of the classes described above for another.

Acid addition salts of the polypeptide or variant polypeptide or of amino residues of the polypeptide or variant polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

E. Methods of the Invention

The invention provides a method to diagnose individuals who are at a greater risk of deleterious consequences due to bacterial infection, e.g., the individuals may be more susceptible to infection by gram-negative bacteria, e.g., local gram-negative infection, more susceptible to sepsis induced by gram-negative bacteria, more susceptible to chronic airway disease, more susceptible to asthma, more susceptible to gall bladder disease, more susceptible to pyelonephritis, more susceptible to pneumonia, more susceptible to bronchitis, more susceptible to chronic obstructive pulmonary disease, more susceptible to arthritis, at higher risk for severe cystic fibrosis, and more susceptible to local and systemic inflammatory conditions such as systemic inflammatory response syndrome (SIRS), and acute respiratory distress syndrome (ARDS). The invention is also useful in the development of drugs that target the TLR4 gene product, e.g., increase or decrease the function of TLR4, especially the extracellular domain. These agents may thus be useful to prevent or ameliorate infection by gram-negative bacteria, prevent or ameliorate sepsis induced by gram-negative bacteria, prevent or ameliorate LPS-induced chronic airway disease in normal, cystic fibrosis and asthmatic populations, prevent or ameliorate arthritis, and prevent or ameliorate local and systemic inflammatory conditions such as SIRS and ARDS, particularly in individuals at risk for these indications or conditions.

The invention will be further described by the following non-limiting examples.

EXAMPLE 1

Methods

Study Subjects. The study population consisted of 83 healthy adult volunteers (31 men, 52 women) aged 18–50. Exclusion criteria included any history of allergies, tobacco use, cardiac or pulmonary disease. After written informed consent was obtained, all subjects were screened with spirometry, inhalation challenge with histamine, skin testing for common aeroallergens, chest x-ray, and electrocardiogram. All participants had normal screening studies (including histamine $PC_{20}$>32 mg/ml), were on no medications (except birth control), and had no significant acute or chronic cardiopulmonary disease or occupational exposures.

Inhalation Challenge Protocol. All subjects were exposed by inhalation challenge to buffered sterile saline (HBSS) followed by increasing concentrations of LPS. The solutions were delivered via a DeVilbiss 646 nebulizer powered by compressed air at 30 psi (DeVilbiss Co., Somerset, Pa.) and a Rosenthal dosimeter (Laboratory for Applied Immunology, Baltimore, Md.). After the HBSS, subsequent inhalations delivered in increasing doses of LPS according to the following schedule: 0.5 μg, 1.0 μg, 2.0 μg, 3.0 μg, 5.0 μg, 10 μg, and 20 μg. Thus, the entire protocol delivered a total of 41.5 μg of LPS.

Incremental LPS inhalation challenge. The incremental LPS inhalation challenge was performed as follows. The % decline in $FEV_1$/μg LPS was calculated following administration of the cumulative LPS dose that either resulted in at least a 20% decline in $FEV_1$ or the decline in $FEV_1$ following a cumulative inhaled dose of 41.5 μg of LPS. Subjects above the x-axis (solid bars in FIG. 5) are homozygous for the wild type allele (WT/WT); subjects below the x-axis (open bars in FIG. 5) are either heterozygous or homozygous (*) for the missense Asp299Gly allele. The data is replotted in the inset after the values for the dose-response slope were log normalized. P values are presented for the comparison of the % decline in $FEV_1$/μg LPS between subjects with the WT/WT genotype (N=73) and those with at least one Asp299Gly allele (N=10) using absolute values (P=0.037) and log normalized values (P=0.026). Since the distribution of the dose-response slope (% decline $FEV_1$/cumulative dose of inhaled LPS) was highly skewed, the two-sample Monte-Carlo permutation test based on 10,000 permutations was used to calculate P values (Fisher et al., 1993). To assess the allelic frequency of TLR4 sequence variants, a well-characterized Iowa population (Lidral et al., 1998) and the Centre d'Etude du Polymorphisme Humain (CEPH) population (NIH-CEPIT, 1992) were screened for specific sequence variants identified in the 83 study subjects.

Endotoxin. Solutions of endotoxin for inhalation were prepared according to a standard protocol using lyophilized *Escherichia coli* (serotype 0111:B4, Sigma Chemical Co., St. Louis, Mo.) LPS. These solutions of LPS were resuspended in sterile Hank's balanced salt solution (without calcium or magnesium) at a pH of 7.0 and filter sterilized. All solutions used for inhalation were tested for sterility (bacteria and fungi) and LPS content (*Limulus amebocyte* lysate assay, QCL-1000; Whittaker Bioproducts, Walkersville, Md.) prior to separation into individual aliquots. These aliquots were stored immediately after preparation at −70° C. until used.

Physiologic Measurements. A Spirotech (Atlanta, Ga.) S600 spirometer was used to assess pulmonary function; spirometry was performed using standards established by the American Thoracic Society. Subjects were positioned upright in a chair and were using noseclips. Baseline spirometry was recorded after inhalation of saline, and then 1, 10, 20, and 30 minutes following inhalation of each dose of LPS, and compared with the post-saline baseline spirometry. If the study subject's $FEV_1$ was greater than 80% of the baseline measurement at the final assessment (30 minutes post-saline), the inhalation challenge was continued and the next does of LPS was administered. The challenge test was terminated when any of the following criteria had been met: 1) the subject did not wish to continue for any reason; 2) the subject's FEV, decreased 20% or greater from baseline; or 3) a cumulative dose of 41.5 μg had been achieved. Of 84 subjects enrolled in the study, 1 subject withdrew prior to completion of the LPS inhalation challenge test, 52 subjects had at least a 20% decline in the $FEV_1$ during the LPS inhalation challenge test, and 31 subjects inhaled a cumulative dose of 41.5 μg of LPS and did not decrease their $FEV_1$ by 20%.

Assignment of Phenotype. Study subjects were categorized as either "responsive" or "hyporesponsive" to inhaled LPS. In the course of previous investigations, a large number of study subjects have been exposed to inhaled LPS (Jagielo et al., 1996; Deetz et al., 1997). In general, most healthy non-asthmatic study subjects develop airflow obstruction ($FEV_1 \leqq 80\%$ of the pre-exposure value) when challenged with approximately 40 μg of LPS. Based on this and a standard approach to the definition of airway hyperreactivity ($FEV_1$ decline of 20% from pre-exposure values) (Chai et al., 1975), subjects were categorized as "LPS responsive" if they decreased their $FEV_1$ by at least 20% at any point during the LPS inhalation challenge, or "hyporesponsive" if they had <20% decline in their $FEV_1$ after inhaling a cumulative does of 41.5 μg of LPS.

Isolation of Genomic Clone. A human bacterial artificial chromosomal (BAC) library (Research Genetics; Huntsville, Ala.) was screened with two sets of primers (1F: 5'ATGGGGCATATCAGAGCCTA 3; SEQ ID NO:8, IR: 5'GTCCAATGGGGAAGTTCTCT 3; SEQ ID NO:9, 2F: 5'TCATTGTCCTGCAGAAGGTG 3; SEQ ID NO:10, and 2R: 5'CAGGGCTTTTCTGAGTCGTC 3; SEQ ID NO:11) derived from the human TLR4 gene (Genbank Accession Nos. U88880 and U93091). These sets of primers amplified a 160 bp and 140 bp product, respectively. PCR reactions were prepared by combining the following components: 1 μl of PCR 10× buffer (100 mM Tris-HCl, pH 8.3, 500 mM KCl), 200 μM each of dCTP, dGTP, DATP, and dTTP, 0.25 μM of each primer, 0.2 U of AmpliTaq DNA polymerase (Perkin Elmer; Norwalk, Conn.) and 1 μl of the library sample in a final volume of 10 μl. Thermal cycling was performed with an initial denaturation at 94° C. for 3 minutes followed by 35 cycles comprising 94° C., 55° C., and 72° C. steps of 30 seconds each and a final extension of 72° C. for 5 minutes. PCR products were separated by electrophoresis on 2% agarose gels, stained with ethidium bromide and visualized under UV light.

Mutation Detection. Genomic DNA was isolated from whole blood obtained from the study subjects using a rapid salt isolation procedure (Laitinen et al., 1994). Overlapping primer sets were designed across the coding sequence such that products did not exceed 250 bp (Table 1). Primers were derived from flanking intronic sequences to include all splice sites. PCR reactions were prepared as described above except that 10–20 ng of genomic DNA was used at template. Amplification products were separated on non-denaturing, fan-cooled gels containing 5% acrylamide/bis (19:1), 0.5× TBE, and 2.5% glycerol for 3 hours at 20 W. A subset of PCR products were also run on MDE gels. The gels were subjected to silver staining and aberrant bands extracted from the gel, reamplified, and sequenced in both directions. To verify the sequence of the aberrant band, the same primers were used to amplify and sequence genomic DNA from each subject. At least one individual without the aberrant band was also sequenced for comparison. Amplification products derived from the extracted DNA were purified using spin columns (Qiagen; Santa Clarita, Calif.) and DNA concentration determined by spectrophotometry. The DNA sequence was determined with a Model 377 automated DNA sequencer (Perkin Elmer; Norwalk, Conn.).

TABLE 1

Primers for amplification of TLR4 coding region.

| Exon | 5' NT[a] | FORWARD PRIMER (5'-3') | 5' NTa | REVERSER PRIMER (5'-3') | SIZE (bp) |
|---|---|---|---|---|---|
| 1 | 24 | CTGCTCGGTCAAACGGTGAT[1] | +33 | AGTCAGCTCCTCTGAACTTTC[2] | 206 |
| 2 | −106 | CAGCAAGCACGATATTGGAT[3,b] | +18 | CGTGCTCAGCATTCTAACCT[4,b] | 244 |
| 3 | −53 | GAGTTGGGAGACCATGCAGT[5] | +41 | GAACACCTCACCTTGTGCAG[6] | 262 |
| 4 | −52 | GGTTCTTATTCAGCAGAAAT[7] | 483 | CTTGATAGTCCAGAAAAGGCT[8] | 172 |
| 4 | 496 | GGTGGCTGTGGAGACAAATC[9] | 691 | CCGCAAGTCTGTGCAATAAA[10] | 195 |
| 4 | 639 | ACTTGGACCTTTCCAGCAAC[11] | 798 | GTCAGCTTATGAAGCCTAATTTCT[12] | 159 |
| 4 | 751 | CTTTATCCAACCAGGTGCA[13] | 952 | CAAATTGCACAGGCCCTCTAGA[14] | 201 |
| 4 | 882 | TGGGAGAATTTAGAAATGAAGGA[15] | 1080 | AAAGTCTTTTACCCTTTCAATAGTCA[16] | 198 |
| 4 | 1032 | TTTCTTCATTTTCCCTGGTGA[17] | 1161 | AGAGATTTGAGTTTCAATGTGGG[18] | 129 |
| 4 | 1129 | TGGACAGTTTCCCACATTGA[19] | 1309 | CTTTAGGCTGGTTGTCCCAA[20] | 180 |
| 4 | 1262 | TTCAAAGGTTGCTGTTCTCAAA[21] | 1426 | TGAAAACTCACTCATTTGTTTCAA[22] | 164 |
| 4 | 1349 | TCAAACTTCTTGGGCTTAGAACA[23] | 1526 | CTTCGAGACTGGACAAGCCA[24] | 177 |
| 4 | 1480 | CAGAGTTGCTTTCAATGGCA[25] | 1614 | GAGAGGTCCAGGAAGGTCAA[26] | 134 |
| 4 | 1551 | TCCAGGAAAACTTCCTTCCA[27] | 1746 | ACCTGGAGGGAGTTCAGACA[28] | 195 |
| 4 | 1702 | TTCATTGGATACGTTTCC[29] | 1905 | AAGAGCTGCCTCTGGTCCTT[30] | 203 |
| 4 | 1863 | ACCAGAGTTTCCTGCAATGG[31] | 2032 | TACAAGCACACTGAGGACCG[32] | 169 |
| 4 | 1956 | TGCCTGTGCTGAGTTTGAAT[33] | 2100 | TTTATGCAGCCAGCAAGAAG[34] | 144 |
| 4 | 2013 | CGGTCCTCAGTGTGCTTGTA[35] | 2208 | GGAGGCACCCCTTCTTCTAA[36] | 195 |
| 4 | 2149 | CCAGGATGAGGACTGGGTAA[37] | 2338 | GCGGCTCTGGATGAAGTGCT[38] | 189 |

TABLE 1-continued

| | | | | | |
|---|---|---|---|---|---|
| 4 | 2290 | AAGCCGAAAGGTGATTGTTG[39] | 2442 | CTGAGCAGGGTCTTCTCCAC[40] | 152 |
| 4 | 2398 | TATCATCTTCATTGTCCTGCAGA[41] | 2617 | AGATGTTGCTTCCTGCCAAT[42] | 219 |
| 4 | 2406 | TCATTGTCCTGCAGAAGGTG[43] | 2548 | CAGGGCTTTTCTGAGTCGTC[44] | 142 |
| 4 | 2529 | GACGACTCAGAAAAGCCCTG[45] | 2683 | TGAACAAGTGTTGGACCCAG[46] | 154 |
| 4 | 2597 | AATTGGCAGGAAGCAACATC[47] | 2772 | GATTAGCAGCCCTGCATATCT[48] | 175 |

[a]relative to published cDNA sequence of Medzhitov et. al. (1997), Genbank accession #U93091
[b]relative to published cDNA sequence of Rock et al. (1997), Genbank Accession #U88880, since exon 2 is absent in #U93091.
A "-" indicates primer is within intron on the 5' side of amplified exon; a "+" indicates primer is on the 3' side.
[1]SEQ ID NO:12
[2]SEQ ID NO:36
[3]SEQ ID NO:13
[4]SEQ ID NO:37
[5]SEQ ID NO:14
[6]SEQ ID NO:38
[7]SEQ ID NO:15
[8]SEQ ID NO:39
[9]SEQ ID NO:16
[10]SEQ ID NO:40
[11]SEQ ID NO:17
[12]SEQ ID NO:41
[13]SEQ ID NO:18
[14]SEQ ID NO:42
[15]SEQ ID NO:19
[16]SEQ ID NO:43
[17]SEQ ID NO:20
[18]SEQ ID NO:44
[19]SEQ ID NO:21
[20]SEQ ID NO:45
[21]SEQ ID NO:22
[22]SEQ ID NO:46
[23]SEQ ID NO:23
[24]SEQ ID NO:47
[25]SEQ ID NO:24
[26]SEQ ID NO:48
[27]SEQ ID NO:25
[28]SEQ ID NO:49
[29]SEQ ID NO:26
[30]SEQ ID NO:50
[31]SEQ ID NO:27
[32]SEQ ID NO:51
[33]SEQ ID NO:28
[34]SEQ ID NO:52
[35]SEQ ID NO:29
[36]SEQ ID NO:53
[37]SEQ ID NO:30
[38]SEQ ID NO:54
[39]SEQ ID NO:31
[40]SEQ ID NO:55
[41]SEQ ID NO:32
[42]SEQ ID NO:56
[43]SEQ ID NO:33
[44]SEQ ID NO:57
[45]SEQ ID NO:34
[46]SEQ ID NO:58
[47]SEQ ID NO:35
[48]SEQ ID NO:59

Multi-tissue cDNA Expression Screen. Human adult (Clontech #K1420-1; Palo Alto, Calif.) and fetal (Clontech #K1425-1; Palo Alto, Calif.) multi-tissue cDNA panels were screened by PCR using primers derived from exon 1 (forward; 5'GCTCACAGAAGCAGTGAGGA 3'; SEQ ID NO:60) and exon 4 (reverse; 5'TAGGCTCTGATATGCCCCAT3'; SEQ ID NO:61) of the human TLR4 gene. These PCR experiments were performed in 10 μl reactions composed of 0.025 U/μl of DNA polymerase (BioXACT; Bio-Line; Reno, Nev.), 1.0 μM of each primer, 200 μM of each dNTP, 1 μl of 10× buffer supplied by the manufacturer, and 1 μl of the cDNA sample. PCR conditions were: 95° C. for 2 minutes; cycles of 0.5 minutes at 94° C., 0.5 minutes at 55° C., and 1 minute at 68° C.; followed by a final extension step for 10 minutes at 68° C. The amplified products were separated on a 2% agarose gel, stained with ethidium bromide, and visualized under UV light.

Statistical Analysis. The statistical analysis was designed to determine whether specific mutations in the TLR4 gene were associated with the airway hyporesponsiveness to inhaled LPS. A on-tailed test of statistical significance was employed (Fleiss, 1986). In a 2×2 analysis, a Fisher's one-tailed exact test was used to determine whether specific mutations of the TLR4 gene occurred more frequently in study subjects who were considered LPS hyporesponsive compared to those with a normal airway response to inhaled LPS. In addition, because of the nonparametric distribution of dose-response slope (percent decline $FEV_1$/cumulative dose of inhaled LPS), this outcome log was transformed and the Student's one-tailed T test (assuming unequal variances) was used to determine whether the dose-response slope was significantly less in subjects with a specific mutation of TLR4 compared to subjects with the common TLR4 allele.

Bioassays. Cells were maintained in F12 media supplemented with 10% fetal calf serum (Gibco, Rockville, Md.), 2 mM L-glutamine, and 10,000 units penicillin/streptomycin, with 1 μg/ml of G418 as selective antibiotic. Cells were transfected with a mixture of 4 μg of DNA and 10 μl of Superfect (Qiagen, Valencia, Calif.) for a 35 $mm^2$ dish. The DNA mix consisted of 2 μg of DNA and 10 μg NFκB reporter plasmid encoding for the luciferase gene (Clontech, Palo Alto, Calif.) and 1 μg of each TLR4 (Medzhitov et al., 1997; Genbank #U93091) expression plasmid (WT or Asp299Gly). If only one expression plasmid was used, empty vector pcDNA3.1$^+$ was added to keep the DNA concentration constant. Twenty-four hours later the cells were stimulated with 100 ng/ml of LPS for 6 hours. Total luciferase activity was measured using a commercially available method (Tropix, Bedford, Mass.). Briefly, after rising with PBS, cells were removed from filters by incubation with 120 μl lysis buffer (25 mM Tris-phosphate, pH 7.8; 2 mM DTT; 2 mM 1,2-diaminocyclohexane-N,N,N',N'-tetraacetic acid; 10% glycerol; and 1% Triton X-100) for 15 minutes. Light emission was quantified in a luminometer (Analytical Luminescence Laboratory, San Diego, Calif.).

Figure 6A:
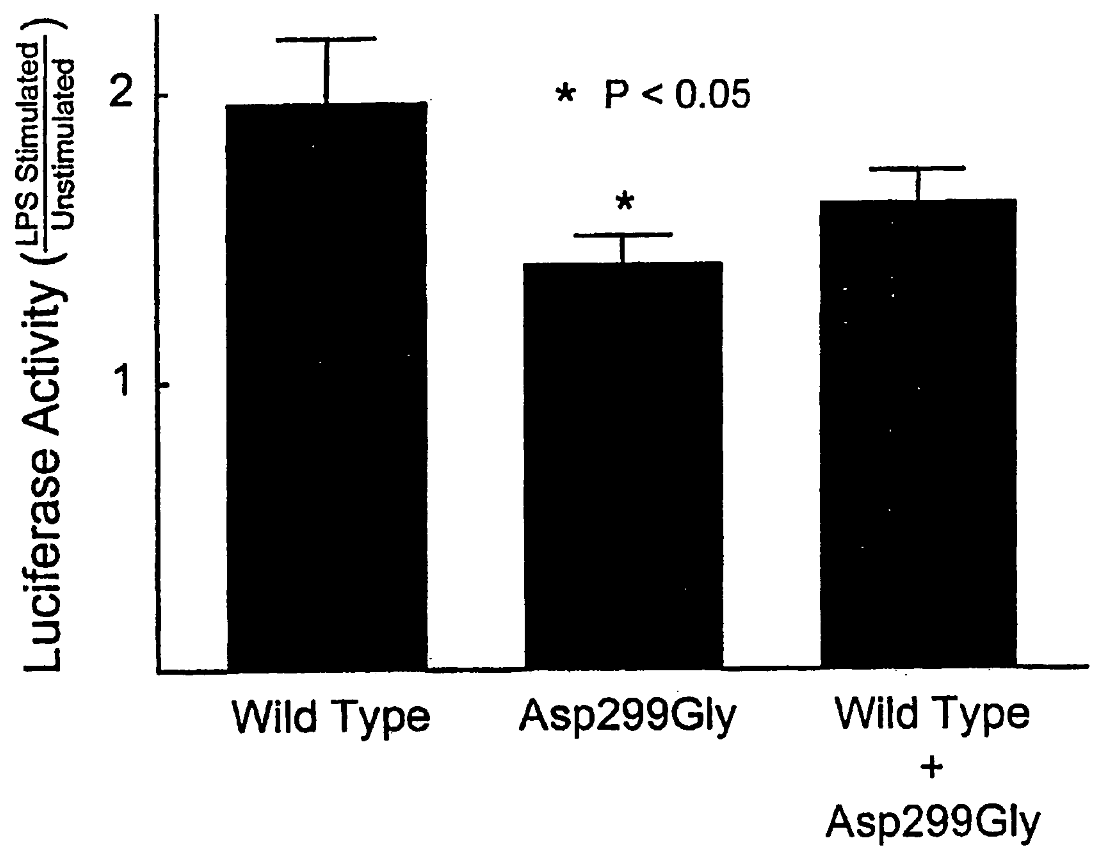
FIG. 6. A) CHO/CD-14 cells that express the CD-14 receptor (generous gift of Doug Golenbock) were transfected with a wild-type or mutant TLR4 allele, and then exposed to LPS. Cells were co-transfected with a luciferase reporter construct. B) IL-1α levels from airway epithelial cells of individuals which had been genotyped for TLR4. Il-1α levels before and after LPS exposure are shown. C) IL-1α levels from airway epithelial cells from a TLR4 heterozygote (WT/Asp299Gly). The cells were transduced with a recombinant adenovirus which expresses TLR4 (Rock et al., 1998), or a recombinant adenovirus which expresses green fluorescent protein (GFP), and then exposed to LPS. D) TNF-α levels from alveolar macrophage from a TLR4 homozygote (Asp299Gly/Asp299Gly). The cells were transduced with a recombinant adenovirus which expresses TLR4 (Rock et al., 1998), and then exposed to LPS.
Figure 6B:
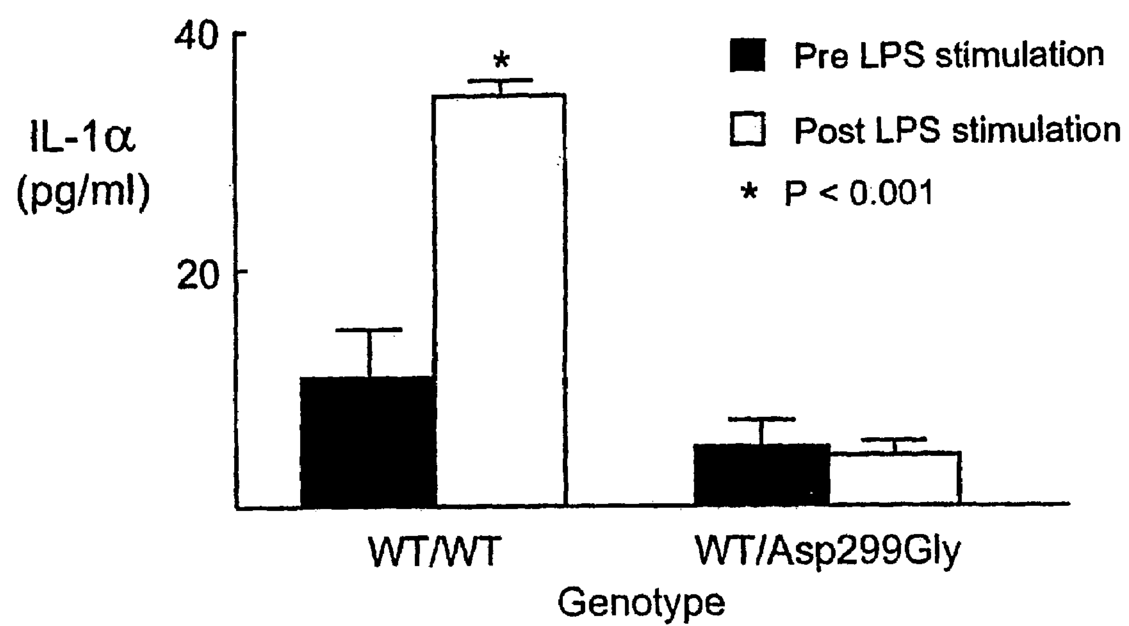

Airway epithelial cells were obtained from trachea and bronchi of lungs removed for organ donation. Cell were genotyped for TLR4 and isolated by enzyme digestion as previously described (Zabner et al., 1996). Freshly isolated cells were seeded at a density of $5\times10^5$ cells/$cm^2$ onto collagen-coated, 0.6 $cm^2$ diameter millicell polycarbonate filters (Millipore Corp., Bedford, Mass.). The cells were maintained at 37° C. in a humidified atmosphere of 5% $CO_2$ and air. Twenty-four hours after plating, the mucosal media was removed and the cells were allowed to grow at the air-liquid interface. The culture media consisted of a 1:1 mix of DMEM/Ham's F12, 5% Ultraser G (Biosepra SA, Cedex, France), 100 U/ml penicillin, 100 μg/ml streptomycin, 1% nonessential amino acids, and 0.12 U/ml insulin. Epithelia were tested for transepithelial resistance, and for morphology by scanning electron microscopy. Fourteen days after seeding, the basal release of IL-1α was measured in WT/WT (12 specimens from 4 individuals) and WT/Asp299Gly (24 specimens from 4 individuals) epithelia by collecting the basolateral conditioned media after 24 hours (FIG. 6*b*). The epithelia were then exposed to 100 ng/ml of LPS on the apical side for 6 hours, and the basolateral media was collected after 24 hours. IL-1α was measured using a commercially available ELISA (R&D; Minneapolis, Minn.).

Figure 6C:
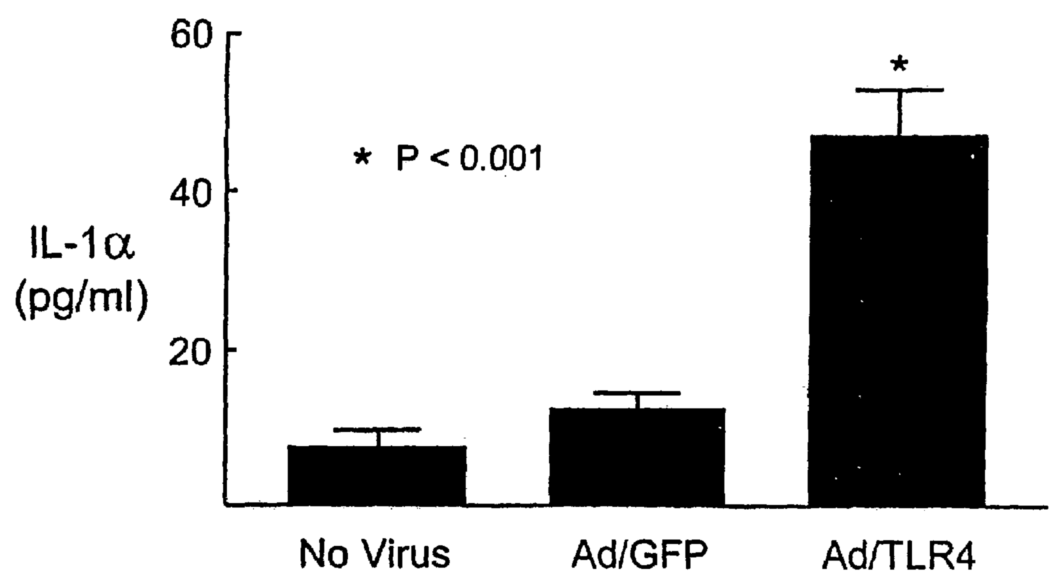
Figure 6D:
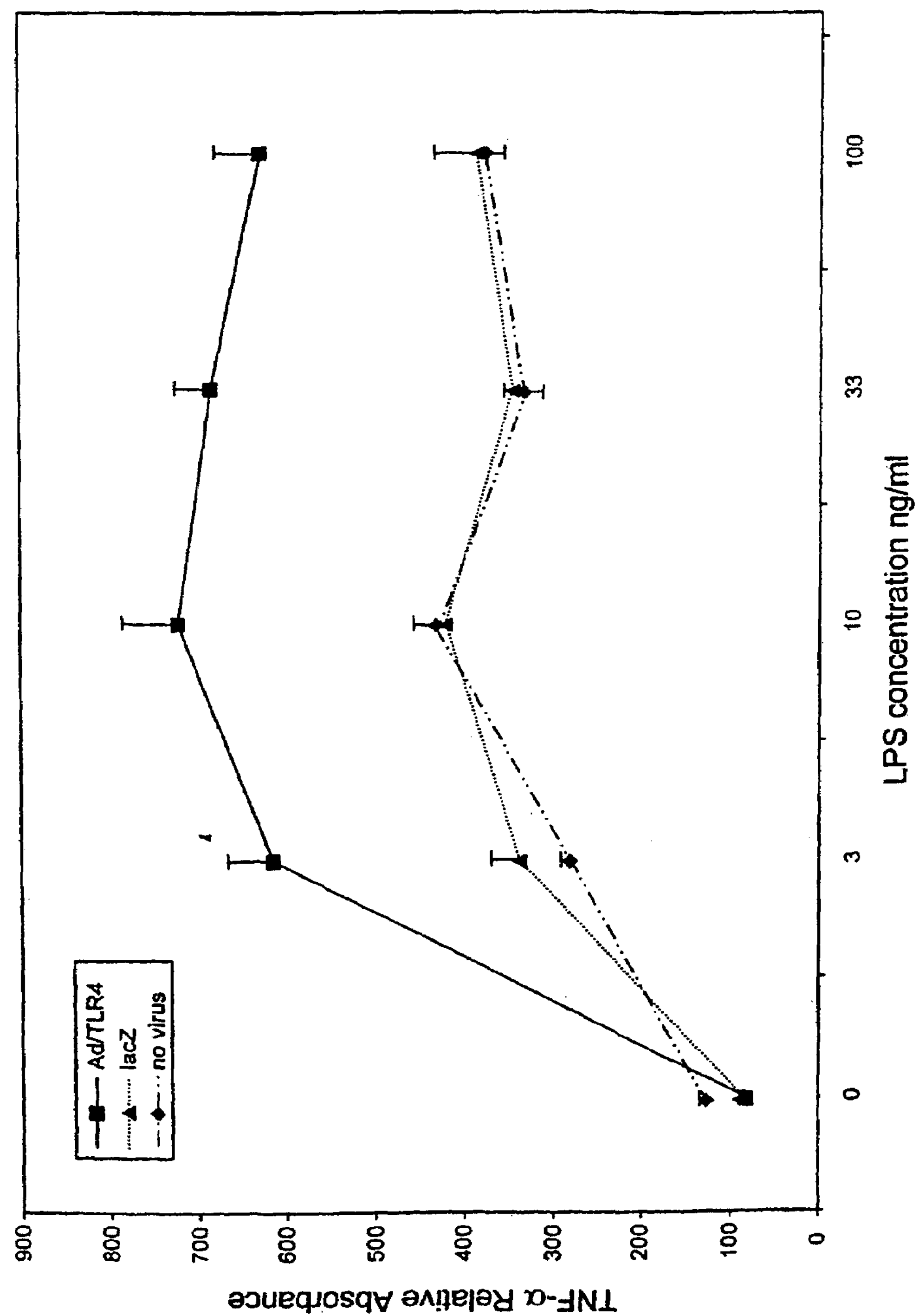

To rescue the LPS hyporesponsive phenotype, heterozygote (WT/Asp299Gly) airway epithelia (FIG. 6*c*) or homozygote (Asp299Gly/Asp299Gly) alveolar macrophages (FIG. 6*d*) were transfected with a recombinant adenovirus vector expressing TLR4 (Rock et al. 1998; Genbank #U88880) that was prepared as described previously (Dandson et al., 1994) by the University of Iowa Gene Transfer Vector Core at titers of about $10^{10}$ infectious units (I.U.)/ml. Briefly TLR4 plasmid was blunt ended and cloned into the shuttle vector pAd5/CMVk-NpA using the EcoRV site. Fourteen days after seeding of the airway epithelia (20 specimens from 4 individuals), 50 MOI of the recombinant viruses (Ad/TLR4 and Ad/eGFP in phosphate buffered saline) were added to the basolateral surface of the epithelia for 30 minutes (Walters et al., 1999). After infection, the epithelia were incubated at 37° C. for an additional 48 hours before the LPS stimulation assay. To assay for basal LPS response, the media was changed with fresh 500 μl of Ultroser G, and collected after 24 hours to measure the basal IL-1α secretion to the basolateral side. After collecting the basal specimen, the epithelia were exposed to 100 ng/ml of LPS on the apical side for 6 hours, and the media was collected after 24 hours. To assay for gene transfer efficiency, the epithelia was associated with 0.05% trypsin and 0.53 mM EDTA. Fluorescence from 50,000 individual cells was analyzed using fluorescence-activated cell analysis (FACScan, Lysys II software, Becton Dickinson, San Jose, Calif.). The percentage of GFP positive cells ranged between 52% and 76%. Human alveolar macrophages were collected by BAL from a homozygote (Asp299Gly/Asp299Gly) study subject as previously described (Deetz et al., 1967). Macrophages were seeded onto a 96 well plate at a density of $10^5$ cells per well. The cells were infected after 4 hours with Ad/TLR4 in a CaPi coprecipitate (Iasbinder et al., 1998) at an MOI of 50, and a $Ca^{++}$ concentration of 16.8 mM. Sixteen hours after infection, the cells were exposed to LPS in 1% serum for 6 hours, and the media was collected. TNF-α was measured using a commercially available ELISA (R&D; Minneapolis, Minn.).

Results

Genomic Structure of the TLR4 Gene. To determine the genomic structure of the TLR4 gene, a bacterial artificial chromosome (BAC) library was screened by PCR with primers derived from the 5' and 3' ends of the cDNA sequence. Human BAC clone 439F3 was identified with both sets of primers and sequenced to identify exon/intro splice sites using the two published cDNA sequences (Medzhitov et al., 1997; Rock et al., 1998). The TLR4 cDNA published by Medzhitov et al. (1997) (Genbank Accession No. U93091) was missing a 120 bp sequence beginning at nucleotide 136 of the other published cDNA (Rock et al., 1998) (Genbank Accession No. U88880). Assuming this missing sequence represented an alternatively spliced exon, DNA sequencing primers were designed to amplify across the predicted splice junctions. When the genomic sequence (FIG. 9) was compared to the cDNA sequences, the exon/intron junctions were revealed (FIG. 1). The human TLR4 gene is organized into 4 exons that span about 11 kb of genomic DNA. As predicted, the 120 bp sequence missing in the cDNA from Medzhitov et al. (1997) corresponds to exon 2.

Figure 2A:
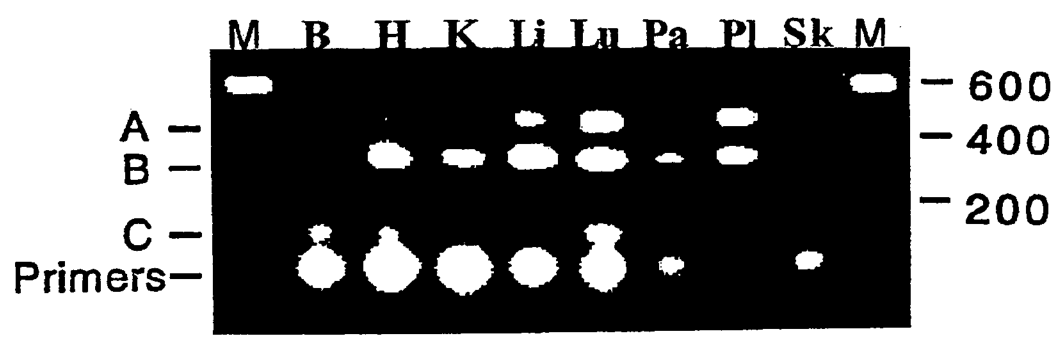
FIG. 2. The human TLR4 gene is alternatively spliced. Photographs are of agarose gels containing the products amplified from a multi-tissue cDNA panel from human adult (panel a; Clontech #K1420-1, Palo Alto, Calif.), and human fetal (panel b; Clontech #K1425-1, Palo Alto, Calif.) cDNA. The tissues included brain (B), heart (H), kidney (K), liver (Li), lung (Lu), pancreas (Pa), placenta (Pl), skeletal muscle (Sk), spleen (Sp), and thymus (T). The first lane of each gel included a 100 bp molecular weight standard (MW). The forward and reverse PCR primers were derived from exons 1 and 4, respectively (see panel c) and amplified three products of 453, 333, and 167 bp. The DNA sequence for these bands showed that both exons 2 and 3 were present in the 453 bp band, that exon 2 was absent in the 333 bp product, and that both exons 2 and 3 were absent in the 167 bp band. The 453 bp and 333 bp sequences are identical to previously published sequences for the human TLR cDNA (Medzhitov et al., 1997; Rock et al., 1998). The open, closed, and shaded boxes indicate the untranslated, translated, and transmembrane domain portions of the TLR4 exons, respectively. The ends of the cDNAs were arbitrarily terminated at the stop codon (STP).
Figure 2B:
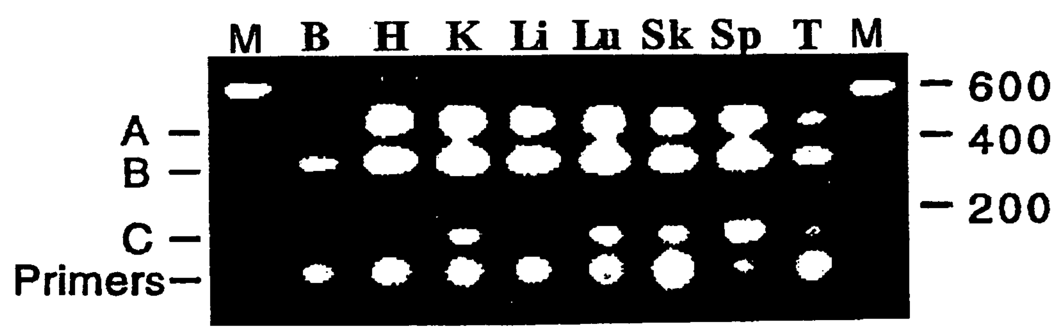
Figure 2C:
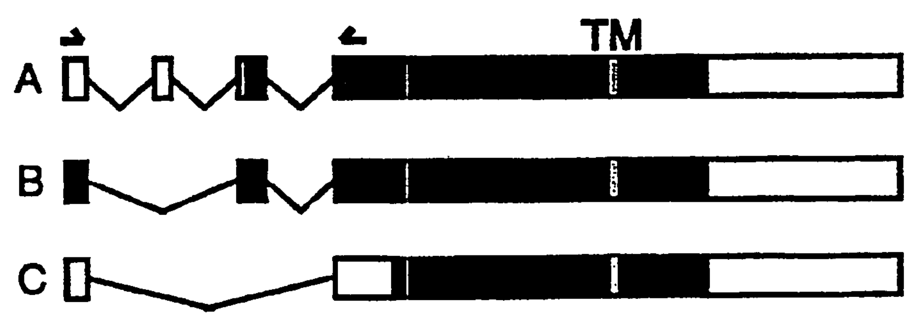

To determine whether other exons may be revealed by additional splice forms, a panel of cDNAs from adult (FIG. 2*a*) and fetal (FIG. 2*b*) tissues were examined with PCR primers designed to amplify all nucleotides between exons 1 and 4. In all adult and fetal tissues, three products were amplified (453, 333, and 167 bp), although their relative amounts varied. In addition to the 3' end of exon 1 and the 5' end of exon 4, the 453 bp product contained both exons 2 and 3, the 333 bp product was missing exon 2, and the 167 bp product was missing both exons 2 and 3 (FIG. 2*c*). The 453 and 333 bp products are identical to the published cDNA sequences (Medzhitov et al., 1997; Rock et al., 1998), and confirm that no other exons are present for the human TLR4 gene. The 167 bp product depicts alternative splicing of exons 1 and 4, and represents a novel TLR4 product. The nucleotide position of alleles are relative to the TLR4 cDNA sequence published by Medzhitov et al. (1997).

Figure 3A:
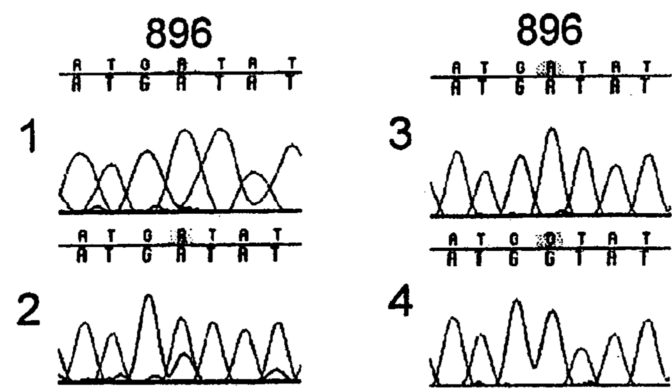
FIG. 3. Mutations in the human TLR4 gene. The SSCV and sequence analysis were performed blinded to the LPS response phenotype of the study subjects. The SSCV gel in panel a contains the products amplified from two samples that are homozygous for the 1060A allele (lanes 1 and 3), a heterozygous sample (lane 2) with both the 896A and 896G alleles, and a homozygous sample (lane 4) with only the 896G allele. The SSCV gel in panel b contains the products amplified from a sample that is homozygous for the T allele at position −11 and the T allele at position 315 (lane 1), and from a sample that is heterozygous with a T and a deletion at position −11 and a T and a C allele at position 315. The nucleotide numbers are based on the previously published TLR4 cDNA sequence (Rock et al., 1998).

Mutation Analysis. SSCV was employed to detect sequence variants across the entire coding region of TLR4 gene in the 83 unrelated probands who completed the incremental LPS inhalation challenge test. When band shifts were detected on SSCV analysis, the bands were sequenced to identify and confirm the sequence variants. The SSCV and sequence analysis were performed blinded to the LPS response phenotype of the study subjects. A band variant was detected by SSCV in 10 (12%) of the 83 subjects, and direct sequencing detected an A to G substitution at nucleotide 896 of the published TLR4 cDNA (FIG. 3*a*) (Genbank Accession No. U88880). To confirm these findings, the 83 unrelated probands were sequenced in the forward and reverse directions with primers designed to amplify the 896 nucleotide; the same 10 individuals were found to have the A896G substitution and the remaining individuals were confirmed to have the common TLR4 allele. Importantly, one of the 10 individuals with the A896G substitution was homozygous for this mutation and the remaining 9 had a single mutant allele. The allelic frequency of the A896G substitution was 6.6% in the study population, 7.9% in a normal control population from Iowa (Lidral et al., 1998), and 3.3% in the parental chromosomes of the CEPH population (NIH-CEPH, 1992).

The A896G substitution results in replacement of a conserved aspartic acid (A) residue with glycine (G) at amino acid 299 (FIG. 4). This missense mutation (Asp299Gly) is in the fourth exon of TLR4 and is present in the extracellular domain of this receptor. The region surrounding amino acid 299 appears to be in an alpha helical conformation (Gibrat et al., 1987). Replacement of the conserved aspartic acid with glycine at position 299 causes disruption of the alpha helical protein structure resulting in the formation of an extended beta strand (Gibrat et al., 1987).

Figure 3B:
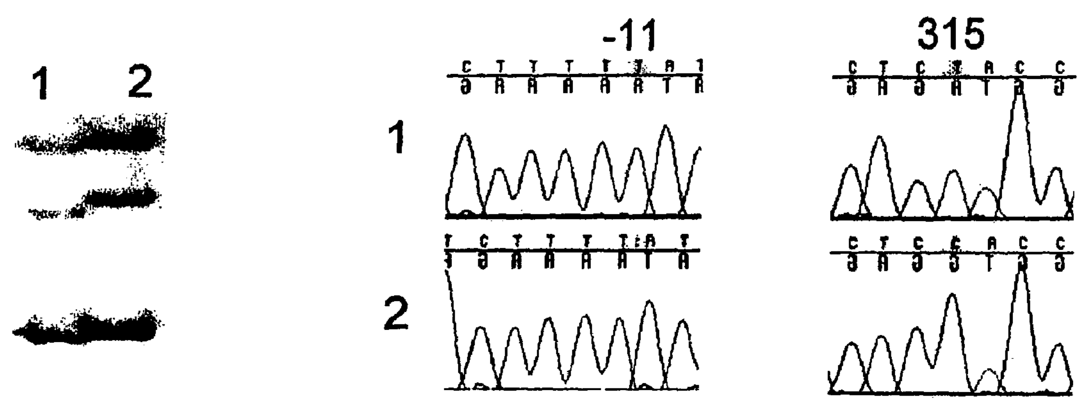

Two other SSCV variants were identified in a single proband; a T to C change at nucleotide 479 (FIG. 3*b*) and a deletion of a thymine nucleotide at position −11 in the third intron. The T479C variant did not alter the amino acid composition and is therefore considered a silent mutation. The T-11 variant did not alter the acceptor splice site, so the significance of this deletion is unknown. The subject with these two sequence variants was responsive to inhaled LPS.

An additional missense mutation was identified within exon 4 of the TLR4 gene. This mutation results in the replacement of a threonine with an isoleucine residue at amino acid 399, which is on the 3' side of the previously identified Asp299Gly mutation. Both mutations are present within the extracellular domain of the TLR4 protein. When the genotypes were compared with the phenotypes associated with endotoxin responsiveness, one individual who carried the Asp299Gly mutation did not carry the Thr399lle mutation. Likewise, one individual who had the Thr399lle mutation did not have the Asp299Gly mutation. Nine of the 83 volunteers carry both mutations. There was a strong correlation between both of the TLR4 mutations and endotoxin hyporesponsiveness.

Figure 5:
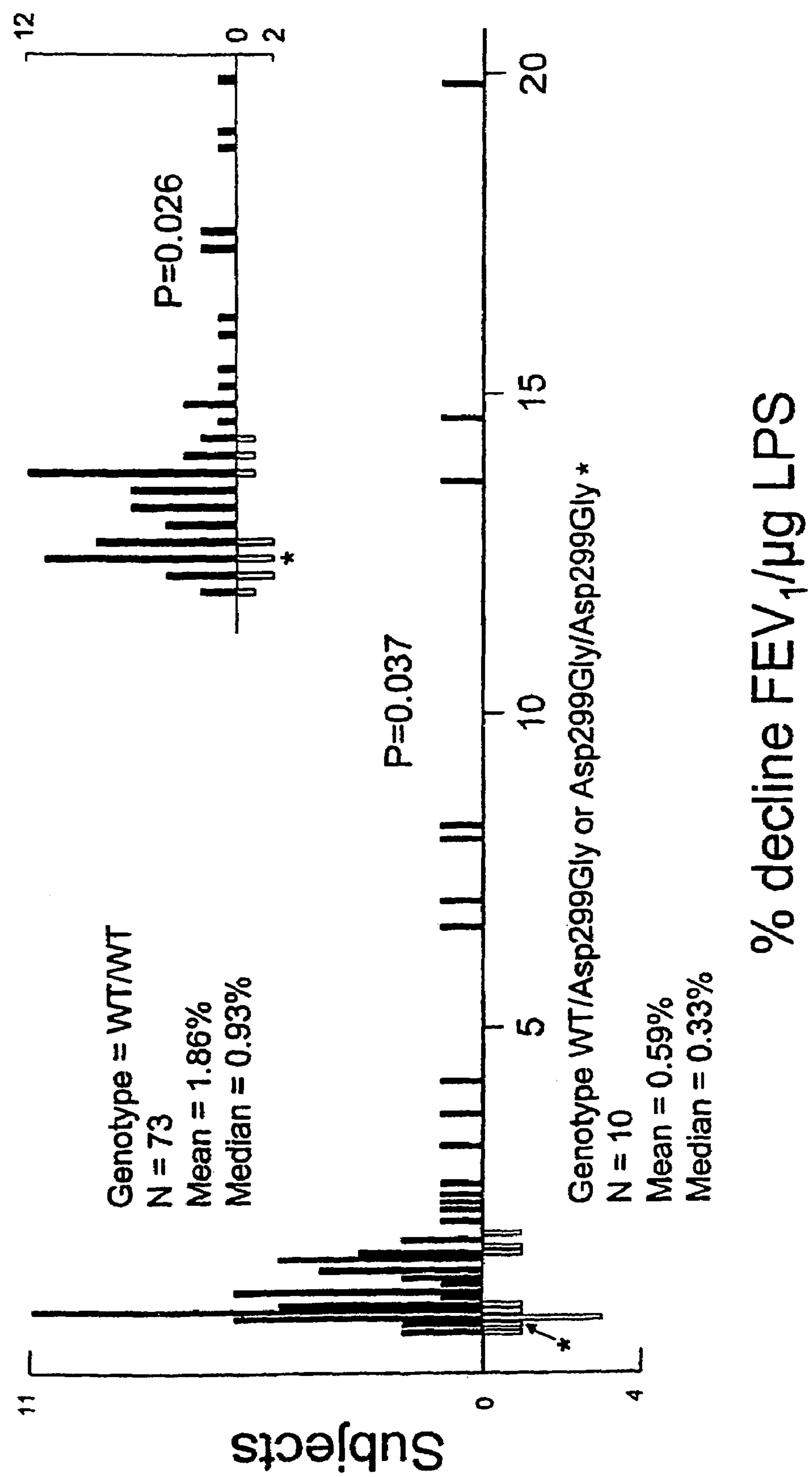
FIG. 5. Frequency distribution histogram of the dose-response slope (% decline in $FEV_1$/μg LPS). The % decline in $FEV_1$/μg LPS was calculated following administration of the cumulative LPS dose that either resulted in at least a 20% decline in $FEV_1$ or the decline in $FEV_1$ following a cumulative inhaled dose of 41.5 μg LPS. Subjects above the x-axis (solid bars) are homozygous for the 896A allele (WT/WT); subjects below the x-axis (open bars) are either heterozygous or homozygous (*) for the missense Asp299Gly allele. The data is replotted in the inset after the values on the x-axis were log normalized. P values are presented for the comparison of the % decline in $FEV_1$/μg LPS between subjects with the WT/WT genotype (N=73) and those with at least one Asp299Gly allele (N=10) using absolute values (P=0.037) and log normalized values (P=0.026). Since the distribution of the dose-response slope (% decline $FEV_1$/cumulative dose of inhaled LPS) was highly skewed, the two-sample Monte-Carlo permutation test based on 10,000 permutations was used to calculate P values (Fisher et al., 1993) the missense mutation (N=10) using absolute values (p=0.04) and the log normalized values (p=0.04) and the log normalized values (p=0.025).

Phenotype/Genotype Analysis. Of the 83 unrelated study subjects who completed the LPS inhalation challenge test, 52 (63%) were responsive to inhaled LPS and 31 (37%) were hyporesponsive to inhaled LPS. When the genotypes of these individuals were examined, the Asp299Gly sequence variant occurred in 3 LPS responsive (5.8%) and 7 LPS hyporesponsive (22.6%) study subjects (P=0.029). Among the subjects with the common TLR4 allele (N=73), the dose-response slope (percent decline $FEV_1$/cumulative dose of inhaled LPS) averaged 1.86% decline in $FEV_1$/μg inhaled LPS (range 0.01%–19.78%), while the dose-response slope for the subjects with the Asp299Gly allele (N=10) was significantly less (P=0.037), averaging 0.59% decline in $FEV_1$/μg inhaled LPS (range 0.00%–1.59%) (FIG. 5). This group difference in the dose-response slope also exists on the log scale (P=0.026) where log ($1+\Delta$ $FEV_1$) was used since one individual has a $\Delta$ $FEV_1$ of 0.0. The subject who was homozygous for the Asp299Gly allele was hyporesponsive to inhaled LPS with a 0.28% decline in $FEV_1$/μg of inhaled LPS. This homozygote Asp299Gly subject is one of a monozygote twin pair; her twin sister was subsequently phenotyped and was also found to be hyporesponsive to inhaled LPS with a 0.34% decline in $FEV_1$/μg of inhaled LPS.

The biological significance of the Asp299Gly mutation was evaluated in several ways. First, transfection of CHO cells with either the WT or the mutant TLR4 gene demonstrated that the mutant allele does not respond normally to LPS stimulation (FIG. 6*a*). Second, airway epithelia obtained from heterozygote (WT/Asp299Gly) individuals do not respond to LPS stimulation (FIG. 6*b*). Third, the wild-type allele of TLR4 clearly restored LPS responsiveness in either airway epithelial cells (FIG. 6*c*) or alveolar macrophages (FIG. 6*d*) obtained from individuals with the TLR4 mutation.

Discussion

The results described herein provide the first direct evidence to indicate that a sequence polymorphism in the TLR4 gene is associated with a hyporesponsive LPS phenotype in humans that interrupts LPS signaling. This conclusion is supported by the following findings: 1) unrelated subjects with the Asp299Gly substitution were significantly less responsive to inhaled LPS than those homozygous for the common TLR4 allele; 2) an individual who was homozygous for the Asp299Gly substitution was hyporesponsive to inhaled LPS; 3) a monozygous twin pair, homozygous for the Asp299Gly substitution, demonstrated a very similar response to inhaled LPS; and 4) in vitro studies demonstrate that mutant TLR4 does not respond to LPS stimulation. This conclusion is indirectly supported by the finding in C3H/HeJ mice where a point mutation in intracellular domain of Tlr4 is also associated with LPS hyporesponsiveness (Poltorak et al., 1998; Qureshi et al., 1999). The identified Asp299Gly missense mutation is in the fourth exon of the TLR4 gene and, unlike the C3H/HeJ mutation, is located in the extracellular domain of this receptor. The findings described herein suggest that a specific region in the extracellular domain of TLR4 may play an important role in receptor function and regulation of the innate immune response to LPS in humans.

This discovery may have important ramifications for a broad spectrum of human diseases. First, the Asp299Gly TLR4 substitution is a relatively common mutation, potentially affecting the responsiveness of a substantial portion of the population to LPS. The allelic frequency of the Asp299Gly TLR4 substitution in the three populations screened was between 3.3% and 7.9%, and homozygous individuals were identified in each of the populations. Second, the results described herein provide further support for the role of TLR4 in LPS signaling. A fundamental understanding of LPS signaling will undoubtedly alter approaches to gram-negative sepsis, as well as other diseases thought to be mediated by endotoxin, such as the systemic inflammatory response syndrome (Wang et al., 1995), acute respiratory distress syndrome (Brighan et al., 1986), and asthma or other forms of airway disease caused (Rylander et al., 1989; Schwartz et al., 1995) or exacerbated (Schwartz et al., 1995; Michel et al., 1996) by endotoxin. Identification of the essential components of LPS signaling also provide new therapeutic targets for endotoxin mediated conditions. Third, the specific Asp299Gly TLR4 substitution may provide a simple screening mechanism to risk stratify a population. Identification of this mutation may lead to a better appreciation of the role of LPS responsiveness in a broad range of acquired and genetic disorders. For example, mutations of the TLR4 gene may explain why a minority of patients with gram-negative sepsis develop ARDS (Hudson et al., 1995) or why patients with cystic fibrosis and the identical CFTR mutation have different courses of disease (Veeze et al., 1994). Finally, it must be acknowledged that normal responsiveness to endotoxin is an important component of innate immunity, and the Asp299Gly TLR4 substitution may prove to be associated with negative clinical outcomes. In fact, the C3H/HeJ mouse is more susceptible to *Salmonella typhimurium* (O'Brien et al., 1980), despite its resistance to LPS (Sultzer et al., 1968). Although individuals with the Asp299Gly TLR4 substitution may be more resistant to localized forms of endotoxin-induced inflammation, these individuals may prove to be more susceptible to a systemic inflammatory response initiated or exacerbated by endotoxin.

The findings described herein demonstrate that a specific region in the extracellular domain of TLR4 plays an important role in receptor function and regulation of the innate immune response to LPS in humans. The sequence variants reported thus far for mammalian, i.e., murine, TLR4 are located in the cytoplasmic domain (Poltorak et al., 1998; Qureshi et al., 1999). While it is logical to hypothesize that mutations in the cytoplasmic domain of TLR4 disrupt the signaling pathway leading to activation of NF-κB and AP-1 (Medhitov et al., 1998), the potential mechanisms that are altered by mutations in extracellular domain of TLR4 are less obvious.

TLR4 is a transmembrane protein and it is therefore not surprising to find a putative signal peptide at the N-terminus, presumably responsible for proper trafficking to the cell membrane (Medzhitov et al., 1997). This finding raises the possibility that sequence variants in the extracellular domain of TLR4 can disrupt trafficking of this receptor to the cell membrane and enhance proteolysis. There are several examples in the literature which show that the presence of a single point mutation at a conserved amino acid can disrupt protein folding and specifically affect protein trafficking (Jackson et al., 1998; DeFranco et al., 1998). Mutations of this kind could give rise to a range of phenotypes from almost normal to completely unresponsive, depending on the severity of the trafficking defect. Another possible mechanism that may explain the association between a mutation in the extracellular domain of TLR4 and LPS responsiveness is impairment of ligand binding to the extracellular domain. The extracellular domains of the toll proteins are clearly involved in the cellular response to LPS (Medzhitor et al., 1997; Yang et al., 1998). Yet, so far no convincing evidence has been found that the toll proteins are directly interacting with LPS (Wright, 1999). The discovery of an association between a mutation in the extracellular domain of TLR4 and a discernable LPS phenotype in humans should aid in clarifying whether the extracellular domain of this receptor is important for proper membrane localization of TLR4 and if LPS directly interacts with TLR4. A final possibility is that the missense mutation of TLR4 affects its interaction with either an extracellular ligand or an intracellular protein (Wright, 1999). The extracellular domain of TLR4, and specifically the Asp299Gly amino acid change may provide a key therapeutic target to modulate LPS signaling.

TLR4 may be one of several factors that may regulate the airway response to inhaled LPS. Among the subjects with the Asp299Gly substitution, 7 were hyporesponsive to LPS and 3 developed airflow obstruction during the LPS inhalation challenge test. None of the subjects with this mutation were in the most sensitive quartile of the LPS responders. Although asthmatic patients were included because of their increased airway responsiveness to inhaled LPS (Michel et al., 1989), it remains possible that the 3 subjects with the Asp299Gly substitution who were responsive to inhaled LPS had some type of airway inflammation (e.g., early viral illness) that enhanced their response to inhaled LPS. Moreover, since 22.6% of the study subjects who were hyporesponsive to LPS had at least one copy of the Asp299Gly TLR4 allele, other genes (or possibly acquired conditions) may prove to play a role in modulating the biological response to LPS. For instance, TNF-α is one of the primary cytokines that mediates the toxic effects of LPS (Beutler et al., 1985). A polymorphism at −308 in the TNF-α promoter region results in higher constitutive and inducible levels of TNF-α (Wilson et al., 1997), and this polymorphism has been shown to result in a worse outcome in children with either meningococcal disease (Nadel et al., 1996) or cerebral malaria (McGuire et al., 1994). Likewise, allelic variants of TLR4 receptors and their ligands appear to delay the progression of disease in patients with HIV infection (Mummidi et al., 1995). Thus, TLR4 appears to represent only one of a number of genetic variants that may modulate the pathophysiologic response to LPS

EXAMPLE 2

Methods

To genotype patients for TLR4, a PCR based RFLP assay was employed. For example, to detect point mutations in codon 299 such as those that result in an amino acid substitutions at amino acid 299 (Asp (GAT) to Gly (GGT) change) and/or in codon 399 (Thr (ACC) to Ile (ATC) change), a primer spanning that codon and a second primer 3' or 5' to that primer are prepared. Primers useful to detect a nucleotide change at codon 299 are: 299Forward primer (5' GATTAGCATACTTAGACTACTACCTCCATG 3'; SEQ ID NO:66) and 299Reverse primer (5' GATCAACTTCTGAAAAAGCATTCCCAC; SEQ ID NO:67). The underlined base in the forward primer fortuitously creates a NcoI (CCATGG) restriction site in the context of a mutation which is specific for carriers of the 299 mutation Asp to Gly. Primers useful to detect a nucleotide change at codon 399 include: 399Forward primer (5' GGTTGCTGTTCTCAAAGTGATTTTGGG AGA A; SEQ ID NO:68) and 399Reverse Primer (5' ACCTGAAGACTGGAGAGTGAGTTAAATGCT; SEQ ID NO:69). The underlined base in the 399 Forward primer fortuitously creates a HinfI restriction site (GANTC) in the context of a mutation which is specific for carriers of the 399 mutation Thr to Ile. The reverse primers were chosen at random based solely on such parameters as annealing temperature, expected product size and the like. Additional residues or fewer residues at the 5' end of the primers having the nucleotide change will not affect the outcome as long as the amplification conditions and reverse primers are chosen accordingly.

A MJ Tetrad PTC-225 Thermo cycler was used with both primer sets. For the 299 assay, primers at 10–100 pmole were mixed with 20 ng of genomic DNA, and Perkin Elmer Taq polymerase, deoxyribonucleotides and buffer according to the manufacturer's directions. Cycling conditions included an initial denaturation of 95° C., for 3 to 4 minutes, then 30 cycles of denaturation at 95° C. for 30 seconds; annealing at 55° C. for 30 seconds; and extension at 72° C. for 30 seconds.

For the 399 assay, a Clontech Advantage amplification kit was used according to the manufacturer's directions. The cycling conditions included an initial denaturation at 95° C. for 3 to 4 minutes, then 30 cycles of denaturation at 95° C. for 30 seconds; annealing at 55° C. for 30 seconds; and extension at 72° C. for 30 seconds.

Results

Septic shock remains a significant health concern worldwide and despite progress in understanding the physiologic and molecular basis of septic shock, the high mortality rate of septic shock patients remains unchanged. A common polymorphism in TLR4 was identified that is associated with hyporesponsiveness to inhaled endotoxin or lipopolysaccharide (LPS) in humans (Example 1). Since TLR4 is a major receptor for LPS in mammals and Gram-negative bacteria are the prevalent pathogen associated with septic shock, these specific TLR4 alleles may be associated with a predisposition to or a more severe disease outcome for septic shock patients. Ninety-one septic shock patients as well as 83 healthy blood donor controls were genotyped for the presence of the TLR4 Asp299Gly and TLR4 Thr399Ile mutations. The TLR4 Asp299Gly allele was found exclusively in septic shock patients (P=0.05). Furthermore, septic shock patients with the TLR4 Asp299Gly allele had a significantly higher prevalence of Gram-negative infections. These findings suggest that the TLR4 Asp299Gly allele predisposes people to develop septic shock with Gram-negative organisms.

In another study in a German population, the following observations were made: patients with TLR4 mutation(s) tended to have a longer ICU stay; patients with TLR4 mutation(s) were more prone to sepsis; and sepsis in patients with TLR4 mutation(s) was more severe than in patients that were wild-type for TLR4.

In a third study in a Finnish population, it was observed that mothers of pre-term infants and pre-term infants had a higher frequency of TLR4 mutation(s) than term infants. Also, infants with respiratory distress syndrome (RDS), particularly those born very prematurely, tended to have a higher frequency of mutation(s) than premature infants without respiratory distress syndrome.

Thus, generally, the 299 mutation is slightly more prevalent than the 399 mutation, and in 90% of the cases, both mutations were observed. When only one mutation was found, it was more frequently the 299 mutation.

Thus, the presence of TLR4 mutations is associated with predisposition to septic shock, severity of sepsis, pre-term delivery, and RDS in pre-term infants.

References

Beutler et al., *Science,* 229:869 (1985).
Bonner et al., *Am. J. Respir. Cell Mol. Biol.,* 19:672 (1998).
Brigham et al., *Am. Rev. Respir. Dis.* 133:913 (1986).
Chai et al., *J. Allergy Clin. Immunol.,* 56:323 (1975).
Chow et al., *J. Biol. Chem.,* 274:10689 (1999).
Coutinho et al., *Immunogenetics,* 7:17 (1978).
Davidson et al., *Exp. Neurol.,* 125:258 (1994).
Deetz et al., *Am. J. Respir. Crit. Care Med.,* 155:254 (1997).
DeFranco et al., *Prog. Clin. Biol. Res.,* 397:119 (1998).
De Franco et al., *J. Steroid Biochem. Mol. Biol.,* 65:51 (1998).
Fasbender et al., *J. Clin. Invest.,* 102:184 (1998).
Favorite et al., *J. Clin. Invest.,* 21:589 (1942).
Fisher et al., *Wiley, New York* (1993).
Fleiss, J. C. The design and analysis of clinical experiments. *New Yok:Wiley,* 1986.
Gibrat et al., *J. Mol. Biol.,* 198:425 (1987).
Hoshino et al., *J. Immunol.,* 162:3749 (1999).
Hudson et al., *Am. J. Respir. Crit. Care. Med.,* 151:293 (1995).
Jackson et al., *Thromb. Haemost.,* 80:42 (1998).
Jagielo et al., *Chest,* 110:263 (1996).
Kuhns et al., *J. Immunol.,* 158:3959 (1997).
Laitinen et al., *Biotechniques,* 17:316 (1994).
Lidral et al., *Am. J. Hum. Genet.,* 63:557 (1998).
McGuire et al., *Nature,* 371:508 (1994).
Medzhitov et al., *Cell,* 91:295 (1997).
Medzhitov et al., *Nature,* 388:394 (1997).
Medzhitov et al., *Mol. Cell.,* 2:253 (1998).
Michel et al., *J. Appl. Physiol.,* 66:1059 (1989).
Michel et al., *Rev. Respir. Dis.,* 146:352 (1992).
Michel et al., *Am. J. Respir. Crit. Care Med.,* 154:1641 (1996).
Mummidi et al., *Nat. Med.,* 4:786 (1998).
Nadel et al., *J. Infect. Dis.,* 174:878 (1996).
NIH-CEPH (Collaborative Mapping Group), *Science* 258:67 (1992).
O'Brien et al., *Nature* 287:440 (1980).
Poltorak et al., *Blood Cells Mol. Dis.,* 24:340 (1998a).
Poltorak et al., *Science,* 282:2085 (1998).
Qureshi et al., *J. Exp. Med.,* 189:615 (1999).
Rock et al., *Proc. Natl. Acad. Sci. USA,* 95:588 (1998).
Rylander et al., *Am. Rev. Respir. Dis.,* 140:981 (1989).
Santamaria et al., *J. Immunol.,* 143:913 (1989).
Schwartz et al., *Am. J. Respir. Crit. Care. Med.,* 151:47 (1995a).
Schwartz et al., *Am. J. Respir. Crit. Care. Med.,* 152:603 (1995b).
Sigmund et al., *Hypertension,* 22:599 (1993).
Sultzer, *Nature* 219:1253 (1968).
Vogel et al., *J. Immunol.,* 122:619 (1979).
Veeze et al., *J. Clin. Invest.,* 93:461 (1994).
Walters et al., *J. Biol. Chem.,* 274:10219 (1999).
Wang et al., *Clin. Nucl. Med.,* 20:494 (1995).
Wilson et al., *Proc. Natl. Acad. Sci. USA* 94:3195 (1997).
Wright et al., *Science,* 249:1431 (1990).
Wright et al., *J. Exp. Med.,* 189:605 (1999).
Yang et al., *Nature,* 395:284 (1998).
Zabner et al., *J. Virol.,* 70:6694 (1996).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to detect a polymorphism in a human TLR4 gene, comprising: detecting or determining whether ampliuied TLR4 DNA obtained from a human nucleic acid sample comprises nucleic acid encoding ThR4 polypeptide having an amino acid substitution at residue 299 or 399 of TLR4, wherein the amplified TLR4 DNA is obtained by contacting an amount of the nucleic acid sample with an amount of at least one TLR4-specific oligonucleotide under conditions effective to amplify TLR4 DNA having SEQ ID NO:62, the complement thereof, or a portion thereof, and wherein the TLR4-specific oligonucleotide comprises at least two nucleotide substitutions which result in a restriction site that is indicative of a polymorphism in a human TLR4 gene, which polymorohism results in a TLR4 gene that encodes a TLR4 polypeptide with an amino acid substitution at residue 299 or 399.

2. The method of claim 1 wherein the nucleic acid sample comprises genomic DNA.

3. The method of claim 1 wherein the nucleic acid sample is cDNA.

4. The method of claim 1 wherein the amplified DNA is subjected to electrophoresis.

5. The method of claim 1 wherein the nucleic acid in the sample encodes an amino acid substitution at residue 299.

6. The method of claim 5 wherein the substitution at residue 299 is glycine for aspartic acid.

7. The method of claim 1 wherein the oligonucleotide comprises SEQ ID NO:66 or SEQ ID NO:67.

8. The method of claim 1 wherein the nucleic acid in the sample encodes an amino acid substitution at residue 399.

9. The method of claim 8 wherein the amino acid substitution at residue 399 is isoleucine for threonine.

10. The method of claim 1 wherein the oligonucleotide comprises SEQ ID NO:68 or SEQ ID NO:69.

11. The method of claim 1 wherein at least two TLR4 specific oligonucleotides are contacted with the sample.

12. The method of claim 11 wherein one of the TLR4 specific oligonucleotides is SEQ ID NO:12, SEQ ID NO:18, SEQ ID NO:24, SEQ ID NO:30, SEQ ID NO:36, SEQ ID NO:42, SEQ ID NO:48, SEQ ID NO:54, SEQ ID NO:13, SEQ ID NO:19, SEQ ID NO:25, SEQ ID NO:31, SEQ ID NO:37, SEQ ID NO:43, SEQ ID NO:49, SEQ ID NO:55, SEQ ID NO:14, SEQ ID NO:20, SEQ ID NO:26, SEQ ID NO:32, SEQ ID NO:38, SEQ ID NO:44, SEQ ID NO:50, SEQ ID NO:56, SEQ ID NO:15, SEQ ID NO:21, SEQ ID NO:27, SEQ ID NO:33, SEQ ID NO:39, SEQ ID NO:45, SEQ ID NO:51, SEQ ID NO:57, SEQ ID NO:16, SEQ ID NO:22, SEQ ID NO:28, SEQ ID NO:34, SEQ ID NO:40, SEQ ID NO:46, SEQ ID NO:52, SEQ ID NO:58, SEQ ID NO:17, SEQ ID NO:23, SEQ ID NO:29, SEQ ID NO:35, SEQ ID NO:41, SEQ ID NO:47, SEQ ID NO:53 or SEQ ID NO:59.

13. The method of claim 1 wherein an amino acid substitution at residue 299 or 399 is indicative of a human at risk of or having an indication associated with altered innate immunity.

* * * * *

UNITED STATES PATENT AND TRADEMARK OFFICE

CERTIFICATE OF CORRECTION

PATENT NO. : 7,141,367 B2
APPLICATION NO. : 10/010066
DATED : November 28, 2006
INVENTOR(S) : Schwartz et al.

It is certified that error appears in the above-identified patent and that said Letters Patent is hereby corrected as shown below:

On the Title page, in field (56), under "Other Publications", in column 1, line 11, delete "hyporesponsivenss" and insert --hyporesponsiveness --, therefor.

On the Title page, in field (56), under "Other Publications", in column 2, line 32, delete "Invovlement" and insert -- Involvement --, therefor.

In column 4, line 57, delete "Poitorak et al." and insert -- Poltorak et al. --, therefor.

In column 5, line 24, delete "Il-1$\alpha$" and insert -- IL-1$\alpha$ --, therefor.

In column 8, line 53, delete "NF-kB" and insert -- NF-KB --, therefor.

In column 15, line 32, after "Soc." insert -- , --.

In column 16, line 25, after "5-hydroxylysine," delete "(".

In column 19, line 24, delete "DATP," and insert -- dATP, --, therefor.

In column 22, line 66, delete "on-tailed" and insert -- one-tailed --, therefor.

In column 27, line 36, delete "Medhitov et al." and insert -- Medzhitov et al. --, therefor.

In column 27, line 58, delete "Medzhitor et al." and insert -- Medzhitov et al. --, therefor.

In column 28, line 33, after "LPS" insert -- . --.

In column 30, line 2, delete "De Franco et al." and insert -- DeFranco et al. --, therefor.

In column 30, line 9, delete "New Yok" and insert -- New York --, therefor.

In column 30, line 34, after "Nature" insert -- , --.

In column 30, line 47, after "Nature" insert -- , --.

In column 30, line 53, after "USA" insert -- , --.

In column 67, lines 11–12, in Claim 1, delete "ampliuied" and insert -- amplified --, therefor.

UNITED STATES PATENT AND TRADEMARK OFFICE

CERTIFICATE OF CORRECTION

PATENT NO. : 7,141,367 B2
APPLICATION NO. : 10/010066
DATED : November 28, 2006
INVENTOR(S) : Schwartz et al.

It is certified that error appears in the above-identified patent and that said Letters Patent is hereby corrected as shown below:

In column 67, line 13, in Claim 1, delete “ThR4” and insert -- TLR4 --, therefor.

In column 67, line 23, in Claim 1, delete “polymorohism” and insert -- polymorphism --, therefor.

Signed and Sealed this

Sixth Day of November, 2007

JON W. DUDAS

*Director of the United States Patent and Trademark Office*

SEQUENCE LISTING

<160> NUMBER OF SEQ ID NOS: 72

<210> SEQ ID NO 1
<211> LENGTH: 28
<212> TYPE: DNA
<213> ORGANISM: Homo sapiens

<400> SEQUENCE: 1
gcgtggaggt atgtggctgg agtcagct 28

<210> SEQ ID NO 2
<211> LENGTH: 28
<212> TYPE: DNA
<213> ORGANISM: Homo sapiens

<400> SEQUENCE: 2
tcacggaggt tagaatgctg agcacgta 28

<210> SEQ ID NO 3
<211> LENGTH: 28
<212> TYPE: DNA
<213> ORGANISM: Homo sapiens

<400> SEQUENCE: 3
ttatccaggt aatgaatcca cttttaca 28

<210> SEQ ID NO 4
<211> LENGTH: 21
<212> TYPE: PRT
<213> ORGANISM: Homo sapiens

<400> SEQUENCE: 4

Leu Ala Tyr Leu Asp Tyr Tyr Leu Asp Asp Ile Ile Asp Leu Phe Asn
1 5 10 15

Cys Leu Thr Asn Val
20

<210> SEQ ID NO 5
<211> LENGTH: 20
<212> TYPE: PRT
<213> ORGANISM: Mus musculus

<400> SEQUENCE: 5

Leu Thr Tyr Thr Asn Asp Phe Ser Asp Asp Ile Val Lys Phe His Cys
1 5 10 15

Leu Ala Asn Val
20

<210> SEQ ID NO 6
<211> LENGTH: 20
<212> TYPE: PRT
<213> ORGANISM: Rattus norvegius

<400> SEQUENCE: 6

Leu Thr Tyr Ile Asn His Phe Ser Asp Asp Ile Tyr Asn Leu Asn Cys
1 5 10 15

Leu Ala Asn Ile
20

<210> SEQ ID NO 7
<211> LENGTH: 20

<212> TYPE: PRT
<213> ORGANISM: Cricetulus griseus

<400> SEQUENCE: 7

Phe Thr Tyr Ala Asn Glu Phe Ser Glu Asp Ile Thr Asp Phe Asp Cys
1 5 10 15

Leu Ala Asn Val
20

<210> SEQ ID NO 8
<211> LENGTH: 20
<212> TYPE: DNA
<213> ORGANISM: Homo sapiens

<400> SEQUENCE: 8
atggggcata tcagagccta 20

<210> SEQ ID NO 9
<211> LENGTH: 20
<212> TYPE: DNA
<213> ORGANISM: Homo sapiens

<400> SEQUENCE: 9
gtccaatggg gaagttctct 20

<210> SEQ ID NO 10
<211> LENGTH: 20
<212> TYPE: DNA
<213> ORGANISM: Homo sapiens

<400> SEQUENCE: 10
tcattgtcct gcagaaggtg 20

<210> SEQ ID NO 11
<211> LENGTH: 20
<212> TYPE: DNA
<213> ORGANISM: Homo sapiens

<400> SEQUENCE: 11
cagggctttt ctgagtcgtc 20

<210> SEQ ID NO 12
<211> LENGTH: 20
<212> TYPE: DNA
<213> ORGANISM: Homo sapiens

<400> SEQUENCE: 12
ctgctcggtc aaacggtgat 20

<210> SEQ ID NO 13
<211> LENGTH: 20
<212> TYPE: DNA
<213> ORGANISM: Homo sapiens

<400> SEQUENCE: 13
cagcaagcac gatattggat 20

<210> SEQ ID NO 14
<211> LENGTH: 20
<212> TYPE: DNA
<213> ORGANISM: Homo sapiens

<400> SEQUENCE: 14

-continued

```
gagttgggag accatgcagt                                          20


<210> SEQ ID NO 15
<211> LENGTH: 20
<212> TYPE: DNA
<213> ORGANISM: Homo sapiens

<400> SEQUENCE: 15

ggttcttatt cagcagaaat                                          20


<210> SEQ ID NO 16
<211> LENGTH: 20
<212> TYPE: DNA
<213> ORGANISM: Homo sapiens

<400> SEQUENCE: 16

ggtggctgtg gagacaaatc                                          20


<210> SEQ ID NO 17
<211> LENGTH: 20
<212> TYPE: DNA
<213> ORGANISM: Homo sapiens

<400> SEQUENCE: 17

acttggacct ttccagcaac                                          20


<210> SEQ ID NO 18
<211> LENGTH: 19
<212> TYPE: DNA
<213> ORGANISM: Homo sapiens

<400> SEQUENCE: 18

ctttatccaa ccaggtgca                                           19


<210> SEQ ID NO 19
<211> LENGTH: 23
<212> TYPE: DNA
<213> ORGANISM: Homo sapiens

<400> SEQUENCE: 19

tgggagaatt tagaaatgaa gga                                      23


<210> SEQ ID NO 20
<211> LENGTH: 21
<212> TYPE: DNA
<213> ORGANISM: Homo sapiens

<400> SEQUENCE: 20

tttcttcatt ttccctggtg a                                        21


<210> SEQ ID NO 21
<211> LENGTH: 20
<212> TYPE: DNA
<213> ORGANISM: Homo sapiens

<400> SEQUENCE: 21

tggacagttt cccacattga                                          20


<210> SEQ ID NO 22
<211> LENGTH: 22
<212> TYPE: DNA
<213> ORGANISM: Homo sapiens

<400> SEQUENCE: 22
```

-continued ttcaaaggtt gctgttctca aa 22

<210> SEQ ID NO 23
<211> LENGTH: 23
<212> TYPE: DNA
<213> ORGANISM: Homo sapiens

<400> SEQUENCE: 23
tcaaacttct tgggcttaga aca 23

<210> SEQ ID NO 24
<211> LENGTH: 20
<212> TYPE: DNA
<213> ORGANISM: Homo sapiens

<400> SEQUENCE: 24
cagagttgct ttcaatggca 20

<210> SEQ ID NO 25
<211> LENGTH: 20
<212> TYPE: DNA
<213> ORGANISM: Homo sapiens

<400> SEQUENCE: 25
tccaggaaaa cttccttcca 20

<210> SEQ ID NO 26
<211> LENGTH: 18
<212> TYPE: DNA
<213> ORGANISM: Homo sapiens

<400> SEQUENCE: 26
ttcattggat acgtttcc 18

<210> SEQ ID NO 27
<211> LENGTH: 20
<212> TYPE: DNA
<213> ORGANISM: Homo sapiens

<400> SEQUENCE: 27
accagagttt cctgcaatgg 20

<210> SEQ ID NO 28
<211> LENGTH: 20
<212> TYPE: DNA
<213> ORGANISM: Homo sapiens

<400> SEQUENCE: 28
tgcctgtgct gagtttgaat 20

<210> SEQ ID NO 29
<211> LENGTH: 20
<212> TYPE: DNA
<213> ORGANISM: Homo sapiens

<400> SEQUENCE: 29
cggtcctcag tgtgcttgta 20

<210> SEQ ID NO 30
<211> LENGTH: 20
<212> TYPE: DNA
<213> ORGANISM: Homo sapiens

<400> SEQUENCE: 30
ccaggatgag gactgggtaa 20

<210> SEQ ID NO 31
<211> LENGTH: 20
<212> TYPE: DNA
<213> ORGANISM: Homo sapiens

<400> SEQUENCE: 31
aagccgaaag gtgattgttg 20

<210> SEQ ID NO 32
<211> LENGTH: 23
<212> TYPE: DNA
<213> ORGANISM: Homo sapiens

<400> SEQUENCE: 32
tatcatcttc attgtcctgc aga 23

<210> SEQ ID NO 33
<211> LENGTH: 20
<212> TYPE: DNA
<213> ORGANISM: Homo sapiens

<400> SEQUENCE: 33
tcattgtcct gcagaaggtg 20

<210> SEQ ID NO 34
<211> LENGTH: 20
<212> TYPE: DNA
<213> ORGANISM: Homo sapiens

<400> SEQUENCE: 34
gacgactcag aaaagccctg 20

<210> SEQ ID NO 35
<211> LENGTH: 20
<212> TYPE: DNA
<213> ORGANISM: Homo sapiens

<400> SEQUENCE: 35
aattggcagg aagcaacatc 20

<210> SEQ ID NO 36
<211> LENGTH: 21
<212> TYPE: DNA
<213> ORGANISM: Homo sapiens

<400> SEQUENCE: 36
agtcagctcc tctgaacttt c 21

<210> SEQ ID NO 37
<211> LENGTH: 20
<212> TYPE: DNA
<213> ORGANISM: Homo sapiens

<400> SEQUENCE: 37
cgtgctcagc attctaacct 20

<210> SEQ ID NO 38
<211> LENGTH: 20
<212> TYPE: DNA
<213> ORGANISM: Homo sapiens

<400> SEQUENCE: 38
gaacacctca ccttgtgcag 20

<210> SEQ ID NO 39
<211> LENGTH: 21
<212> TYPE: DNA
<213> ORGANISM: Homo sapiens

<400> SEQUENCE: 39
cttgatagtc cagaaaaggc t 21

<210> SEQ ID NO 40
<211> LENGTH: 20
<212> TYPE: DNA
<213> ORGANISM: Homo sapiens

<400> SEQUENCE: 40
ccgcaagtct gtgcaataaa 20

<210> SEQ ID NO 41
<211> LENGTH: 24
<212> TYPE: DNA
<213> ORGANISM: Homo sapiens

<400> SEQUENCE: 41
gtcagcttat gaagcctaat ttct 24

<210> SEQ ID NO 42
<211> LENGTH: 22
<212> TYPE: DNA
<213> ORGANISM: Homo sapiens

<400> SEQUENCE: 42
caaattgcac aggccctcta ga 22

<210> SEQ ID NO 43
<211> LENGTH: 26
<212> TYPE: DNA
<213> ORGANISM: Homo sapiens

<400> SEQUENCE: 43
aaagtctttt accctttcaa tagtca 26

<210> SEQ ID NO 44
<211> LENGTH: 23
<212> TYPE: DNA
<213> ORGANISM: Homo sapiens

<400> SEQUENCE: 44
agagatttga gtttcaatgt ggg 23

<210> SEQ ID NO 45
<211> LENGTH: 20
<212> TYPE: DNA
<213> ORGANISM: Homo sapiens

<400> SEQUENCE: 45
ctttaggctg gttgtcccaa 20

<210> SEQ ID NO 46
<211> LENGTH: 24
<212> TYPE: DNA

-continued

<213> ORGANISM: Homo sapiens

<400> SEQUENCE: 46
tgaaaactca ctcatttgtt tcaa 24

<210> SEQ ID NO 47
<211> LENGTH: 20
<212> TYPE: DNA
<213> ORGANISM: Homo sapiens

<400> SEQUENCE: 47
cttcgagact ggacaagcca 20

<210> SEQ ID NO 48
<211> LENGTH: 20
<212> TYPE: DNA
<213> ORGANISM: Homo sapiens

<400> SEQUENCE: 48
gagaggtcca ggaaggtcaa 20

<210> SEQ ID NO 49
<211> LENGTH: 20
<212> TYPE: DNA
<213> ORGANISM: Homo sapiens

<400> SEQUENCE: 49
acctggaggg agttcagaca 20

<210> SEQ ID NO 50
<211> LENGTH: 20
<212> TYPE: DNA
<213> ORGANISM: Homo sapiens

<400> SEQUENCE: 50
aagagctgcc tctggtcctt 20

<210> SEQ ID NO 51
<211> LENGTH: 20
<212> TYPE: DNA
<213> ORGANISM: Homo sapiens

<400> SEQUENCE: 51
tacaagcaca ctgaggaccg 20

<210> SEQ ID NO 52
<211> LENGTH: 20
<212> TYPE: DNA
<213> ORGANISM: Homo sapiens

<400> SEQUENCE: 52
tttatgcagc cagcaagaag 20

<210> SEQ ID NO 53
<211> LENGTH: 20
<212> TYPE: DNA
<213> ORGANISM: Homo sapiens

<400> SEQUENCE: 53
ggaggcaccc cttcttctaa 20

<210> SEQ ID NO 54
<211> LENGTH: 20

<212> TYPE: DNA
<213> ORGANISM: Homo sapiens

<400> SEQUENCE: 54
gcggctctgg atgaagtgct 20

<210> SEQ ID NO 55
<211> LENGTH: 20
<212> TYPE: DNA
<213> ORGANISM: Homo sapiens

<400> SEQUENCE: 55
ctgagcaggg tcttctccac 20

<210> SEQ ID NO 56
<211> LENGTH: 20
<212> TYPE: DNA
<213> ORGANISM: Homo sapiens

<400> SEQUENCE: 56
agatgttgct tcctgccaat 20

<210> SEQ ID NO 57
<211> LENGTH: 20
<212> TYPE: DNA
<213> ORGANISM: Homo sapiens

<400> SEQUENCE: 57
cagggctttt ctgagtcgtc 20

<210> SEQ ID NO 58
<211> LENGTH: 20
<212> TYPE: DNA
<213> ORGANISM: Homo sapiens

<400> SEQUENCE: 58
tgaacaagtg ttggacccag 20

<210> SEQ ID NO 59
<211> LENGTH: 21
<212> TYPE: DNA
<213> ORGANISM: Homo sapiens

<400> SEQUENCE: 59
gattagcagc cctgcatatc t 21

<210> SEQ ID NO 60
<211> LENGTH: 20
<212> TYPE: DNA
<213> ORGANISM: Homo sapiens

<400> SEQUENCE: 60
gctcacagaa gcagtgagga 20

<210> SEQ ID NO 61
<211> LENGTH: 20
<212> TYPE: DNA
<213> ORGANISM: Homo sapiens

<400> SEQUENCE: 61
taggctctga tatgccccat 20

<210> SEQ ID NO 62

-continued

<211> LENGTH: 10665
<212> TYPE: DNA
<213> ORGANISM: Homo sapiens
<220> FEATURE:
<221> NAME/KEY: misc_feature
<222> LOCATION: (1)...(10665)
<223> OTHER INFORMATION: n = A,T,C or G

<400> SEQUENCE: 62

```
aaaatactcc cttgcctcaa aaactgctcg gtcaaacggt gatagcaaac cacgcattca     60
cagggccact gctgctcaca aaaccagtga ggatgatgcc aggatgatgt ctgcctcgcg    120
cctggctggg actctgatcc cagccatggc cttcctctcc tgcgtgagac cagaaagctg    180
ggagccctgc gtggaggtat gtggctggag tcagctcctc tgaactttcc ctcacttctg    240
cccagaactt ctcactgtgt gccctggttt gtttattttt gcaaaaaaaa aaagagttaa    300
attaccttaa agactcaaga agccacagag atcaaataat tcattgttac agggcactag    360
aggcagccat tgggggtttg ttccatttgg aaattttgag tgctaacagg ggcatgagat    420
aacatagatc tgcttaaggt ccctgctctg ctaccttgtg gctctgtgaa gaaattatca    480
aacctgtctg agactagttt tcgcatctgt aagagaatta taataccttc ttcactagag    540
agtaagcaga ctgcttcagt gtcatttctt cccactggtg gtctttacac tcagcttcaa    600
gcagtcaccc tgctcctttc aatctcagga aaaagatggc tttgtgtgtg tgtctctaga    660
gaaagaactt tctaagttgg tgcagacttc tgtatgcagt aatatagttt agtccagagg    720
atgaaaaaaa taagagaatg aaaaaggaaa agagagagag agagaagaaa aaagcaagag    780
ggaaatatgt ataatgtcag ctaatgcaac agtttctttc ttagtgaaat accaatcagc    840
tggttggtaa tcttattcat gatggatctc ttttgttttt cccctgcgca gacttcacag    900
ttgctttaga aacccatagt agagccgaac agctaagaaa atgatttaca gtgaggcagg    960
gtcagaaact caagagagaa aaagccagct gcagtcctga agttgaggat ataggagaaa   1020
atcaagtaat atttagcaaa gactaattca ttatcttgaa gccatccctt ccctcaattc   1080
cctgcccata gtcctcctcc ttgtcctctt ctctgnatcc ctctgctgtt aggttaatgg   1140
agatagattt tctaattang ctcactgcga gataaaaccc agcccatgtt tctattagnc   1200
aatattgtct ttgaggctcc atggcttgca ncatttaagc agacatacga atgaagatct   1260
gcatgtttga actctgactt tgcgcatatt acttcatttc tttgaatttc cattttcctc   1320
atctttaaat gcttatttga agattaagtg aaagtatata acaaacaaga actatgcagg   1380
cgtatggtaa gggattaatg atagatgata ataattaatg ttgacatcta ttgatcactt   1440
atactgtagc gggcttttaa ataaactctt taaacacctt atctcattta atccttcaaa   1500
cattctattg gtttcaaaca acagaaaact acaattagct ggcttctgca aggaattttg   1560
ttggaggaaa tgagagcatt cagaaattag atgggagcgt tagagaatta ggcttacaaa   1620
gaatgtggga aagtaggcta gaaagcagtg taaaaacaaa gacagcataa agcacttgac   1680
cttatttact aggttccacc atgggaatcc atgcactcta aagatttccc cctatttcta   1740
catcactttg ctcaagggtc aatgagccaa ggaaaagaat gcagttgtca aaatctgggc   1800
catgactaag gaaggtctgg acatcttgac tgccagacag tctccccaat gatatggagt   1860
atttagaatg atactggata ttttatttat tttttgtatt ttcaactttt aagttcagag   1920
gcacatgtgc agagcatgca ggtttattac ataagtaaat gtgtgccatg gtgatttgct   1980
gcatagatca tgaaaatatg gaacgcatca tggatttgtg tgtcatcctt gtgcaggggc   2040
catgctcatc ttctctgtat ccttccaatt ttagtatatg tgctactgca gcaagcacga   2100
```

-continued

```
tattggatat tttattacct acattttaca tatgataaaa tgaggctcac tgaggttttt   2160
cttttgttcg ttttattttg ttttgttttt aaagacttgg ccctaaacca cacagaagag   2220
ctggcatgaa acccagagct ttcagactcc ggagcctcag cccttcaccc cgattccatt   2280
gcttcttgct aaatgctgcc gttttatcnc ggaggttaga atgctgagca cgtagtaggt   2340
gctctttact ttctaatcta gagtaagaca atttataagc atgaattgag tgaatggatg   2400
gatggatata tggatggaag gatggacaga tggatgaaag gttgactgaa ttttgtgctt   2460
gcacaaaaag aggcccctct ccaccatctc tggtctagga gaggggagtt gggagaccat   2520
gcagtaaaga tacttcatgt catgtgtaat cattgcaggt ggttcctaat attacttatc   2580
aatgcatgga gctgaatttc tacaaaatcc ccgacaacct ccccttctca accaagaacc   2640
tggacctgag ctttaatccc ctgaggcatt taggcagcta tagcttcttc agtttcccag   2700
aactgcaggt gctggattta tccaggtaat gaatccactt ttacatactg cacaaggtga   2760
ggtgttcatt gtcctatcat ttcattattg gactggaaag cttggtttgt ggagtctcat   2820
cttcattcac ttattcattc atacaacaga tgtcttatta actatataac cttgagcaag   2880
ctacctctat tctccaggtc tcagttttct aatctgtgaa gtaggcagtt ggctgagaca   2940
gcttctaagg gcaattctaa ttttaggttt tcttttaaga caggagagaa aattagctta   3000
aattctttca taagcagcta tttattgact acttgctata tgttgtacac tctgcaagaa   3060
gacaggcata tattgatata taacacacag cccctgttgt taaggaggca tatcttcttg   3120
aaagagttaa taccttaaag tcctgggtat ggtcctgggt acatagtata tagtcaacac   3180
attttaatta tgatttttg gatctggaaa ctgatataaa gatagcgaca tataacagta   3240
ggtgataaat tatgtttaaa ctaaaggtaa ctaattgtat ttttcagaag aggggccttc   3300
tctgtggtgg gtagtcaaga aagattcatg aactgcataa gattcaaaca atgtctagaa   3360
tattaaaact agtggtggca ggtgaaatgt catcttgata ttttagggga accaaattct   3420
aaaagggttt tcatcatcgg ggccttattt gcaaatcgaa ctagataatg gatcatgttc   3480
tctgcaatgg tttgtaaaac atttcaaaac attttacata ttttttatta tagaaattat   3540
tgataaagac taaggtcaca gtataaaaat cctttttaga gcagacattt ctgtagaaga   3600
gtgaacatat gacctattat actctaattt ggatatagat aggatgtaac aaaggagtaa   3660
tgggaacaat tcaaaggcag tggtatagtg catanagtcc tgttggggtc agaagacctg   3720
agcccaagtt tacccccaac atttataacc catgtaacct tagcatatta cttcatctcc   3780
cttaatcctt agtttcatat ctgatcaatg gaaatgatga aacttattct gctggattaa   3840
atgtgataat aaatattaat atgctgtata tatttaaatt tttataaaat atattttata   3900
agcataaagt attcttacag aatttcatta ggtttttaaa ataatttcaa cttttatttt   3960
tgattcaggg atttacatgg ttatattgcg taatgctgag gtgtagggta caatcgatac   4020
catcactcag gtagtgagca tagtacccaa tagttagttt ttcaaccctt gctgctttct   4080
ctctatcccc tctctagtaa tccccagggt ctatttttgt catctttatg tccatgtgta   4140
ctccatgttt ggatcctact tataaagtga gaactcatgg tatttggctt tctgtncctt   4200
tgttngctaa tttgcttagg ataatggcta ctagctgcat ctatgccatt atgttctaaa   4260
tttcanttnc ctgcatgaaa attttgtcaa gtactctatt aaggtagacc acctctccct   4320
tttttttca aacaagaagt agnttttccc aaacaatgcc cttatggaat tnatcttcaa   4380
tccnnggata cccaataact tgccccaaan ccttaatctg ncttacagag aggccacctt   4440
```

-continued

```
ccttctgtaa cccataggag atttggattg gtaagaatgc tttgtgatag cccagcagcc   4500
ttctttcccc tatagaaata tatatatant ctttttatag gtgaggaact gaagcttgaa   4560
taatttaaat gacttatata catnatcatt gcttgttagc cacagaccag agatttaagt   4620
tcncatctcc agaatccaac ttaaatgttt tctttgtctt aatactctac ttctctaaag   4680
tgattatcac caatgtaatg atatagagnc acagcaagac cctttccttc tcacctaatg   4740
tatagagcaa tgcagagata gaatgatggg ctataacaat catataattg aaagaaagaa   4800
cttcaaaaat aatcaagttc agctgtttga tttataaatg tgataactaa aacctagaga   4860
ggaaaagagg tactcaagat cacacagtag gagaggactg cagaaacacc aaacccaagc   4920
tcttttgtcc actcttccag cgttctttct actatactgc ctatccttta tctagttacc   4980
aataaataac aaaagcttgg accacaatgc ttttattgtc taggaaactc ctgaagaagc   5040
taaataaaat gggtggggaa tattgtaaat gtaattcagg ctggattaag aaagaactta   5100
tttgacattg taactgacaa gcacctgcaa tgctgaaagg aatttttcat tggcntgctg   5160
tttgctgggc tgcatcaaag ccctgtctct aggacatgtc tctgaacatt gtgtgtagca   5220
tggctttcat ttcttttagg ataaaattca aaacccttta tctggttggt aaacctctgc   5280
ctaattggga accttctttc tccacaactc catattgtac actccaattt catctctgtt   5340
ctccaaccat ggaagctatt tgtcatgatt cctccttgtg tcattttttt tctgtcaacc   5400
ttggggcttt tgtgtttgct gttcacttca cctcctttta ttgttaactt ctactcatct   5460
ttcaattttc aacttaagtg ttctcagaga aacctacttt gattttcttg gtccanaacg   5520
gttctctgga tgtgaactct tatagcacat aattttcact tttttccaca aaactcgctc   5580
ctatcacctg ttacaagcat ttacctctga taacaagaac tttcaaatat ctagctgtca   5640
tgtaagcact tttcataaac attaagagta tctgtgacac ttatgtgtaa tgtttcgtat   5700
ctctgaaatt gatatttacc agtcatttat cttggctacc aactaacaac tatccatatt   5760
atctgtacca atcagatgta taatcacaat tttgtgtgac agaaaatggc taaacttgat   5820
ccaaggctat tacatgcttt atcaactgca caatctttat atatgtcaat tattgatctt   5880
taactgattt ccttcttatg gattttctcc tctgcttatc atgtatgcct aacatgacaa   5940
aaaagagcct atcattgcag ccagtatgat aatactcagt ctgtggggct tcttatttgc   6000
ttattccatc atcatctgtc ctgcttgatg tctttgccta tgcacaatca tatgacccat   6060
cacatctgta tgaagagctg gatgactagg attaatattc tattttaggt tcttattcag   6120
cagaaatatt agataatcaa tgtcttttta ttcctgtagg tgtgaaatcc agacaattga   6180
agatggggca tatcagagcc taagccacct ctctacctta atattgacag gaaaccccat   6240
ccagagttta gccctgggag ccttttctgg actatcaagt ttacagaagc tggtggctgt   6300
ggagacaaat ctagcatctc tagagaactt ccccattgga catctcaaaa ctttgaaaga   6360
acttaatgtg gctcacaatc ttatccaatc tttcaaatta cctgagtatt tttctaatct   6420
gaccaatcta gagcacttgg acctttccag caacaagatt caaagtattt attgcacaga   6480
cttgcgggtt ctacatcaaa tgccccctact caatctctct ttagacctgt ccctgaaccc   6540
tatgaacttt atccaaccag gtgcatttaa agaaattagg cttcataagc tgactttaag   6600
aaataatttt gatagtttaa atgtaatgaa aacttgtatt caaggtctgg ctggtttaga   6660
agtccatcgt ttggttctgg gagaatttag aaatgaagga aacttggaaa agtttgacaa   6720
atctgctcta gagggcctgt gcaatttgac cattgaagaa ttcccgatta gcatacttag   6780
actactacct cgatgatatt attgacttat ttaattggtt gacaaatggt tcttcatttt   6840
```

-continued

```
ccctggtgag tgtgactatt gaaagggtaa aagacttttc ttataatttc ggatggcaac   6900
atttagaatt agttaactgt aaatttggac agtttcccac attgaaactc aaatctctca   6960
aaaggcttac tttcacttcc aacaaaggtg ggaatgcttt ttcagaagtt gatctaccaa   7020
gccttgagtt tctagatctc agtagaaatg gcttgagttt caaaggttgc tgttctcaaa   7080
gtgattttgg gacaaccagc ctaaagtatt tagatctgag cttcaatggt gttattacca   7140
tgagttcaaa cttcttgggc ttagaacaac tagaacatct ggatttccag cattccaatt   7200
tgaaacaaat gagtgagttt tcagtattcc tatcactcag aaacctcatt taccttgaca   7260
tttctcatac tcacaccaga gttgctttca atggcatctt caatggcttg tccagtctcg   7320
aagtcttgaa aatggctggc aattctttcc aggaaaactt ccttccagat atcttcacag   7380
agctgagaaa cttgaccttc ctggacctct ctcagtgtca actggagcag ttgtctccaa   7440
cagcatttaa ctcactctcc agtcttcagg tactaaatat gagccacaac aacttctttt   7500
cattggatac gtttccttat aagtgtctga actccctcca ggttcttgat tacagtctca   7560
atcacataat gacttccaaa aaacaggaac tacagcattt tccaagtagt ctagctttct   7620
taaatcttac tcagaatgac tttgcttgta cttgtgaaca ccagagtttc ctgcaatgga   7680
tcaaggacca gaggcagctc ttggtggaag ttgaacgaat ggaatgtgca acaccttcag   7740
ataagcaggg catgcctgtg ctgagtttga atatcacctg tcagatgaat aagaccatca   7800
ttggtgtgtc ggtcctcagt gtgcttgtag tatctgttgt agcagttctg gtctataagt   7860
tctattttca cctgatgctt cttgctggct gcataaagta tggtagaggt gaaaacatct   7920
atgatgcctt tgttatctac tcaagccagg atgaggactg ggtaaggaat gagctagtaa   7980
agaatttaga agaaggggtg cctccatttc agctctgcct tcactacaga gactttattc   8040
ccggtgtggc cattgctgcc aacatcatcc atgaaggttt ccataaaagc cgaaaggtga   8100
ttgttgtggt gtcccagcac ttcatccaga gccgctggtg tatctttgaa tatgagattg   8160
ctcagacctg gcagtttctg agcagtcgtg ctggtatcat cttcattgtc ctgcagaagg   8220
tggagaagac cctgctcagg cagcaggtgg agctgtaccg ccttctcagc aggaacactt   8280
acctggagtg ggaggacagt gtcctggggc ggcacatctt ctggagacga ctcagaaaag   8340
ccctgctgga tggtaaatca tggaatccag aaggaacagt gggtacagga tgcaattggc   8400
aggaagcaac atctatctga agaggaaaaa taaaaacctc ctgaggcatt tcttgcccag   8460
ctgggtccaa cacttgttca gttaataagt attaaatgct gccacatgtc aggccttatg   8520
ctaagggtga gtaattccat ggtgcactag atatgcaggg ctgctaatct caaggagctt   8580
ccagtgcaga gggaataaat gctagactaa aatacagagt cttccaggtg ggcatttcaa   8640
ccaactcagt caaggaaccc atgacaaaga aagtcatttc aactcttacc tcatcaagtt   8700
gaataaagac agagaaaaca gaaagagaca ttgttctttt cctgagtctt ttgaatggaa   8760
attgtattat gttatagcca tcataaaacc attttggtag ttttgactga actgggtgtt   8820
cactttttcc tttttgattg aatacaattt aaattctact tgatgactgc agtcgtcaag   8880
gggctcctga tgcaagatgc cccttccatt ttaagtctgt ctccttacag aggttaaagt   8940
ctagtggcta attcctaagg aaacctgatt aacacatgct cacaaccatc ctggtcattc   9000
tcgagcatgt tctatttttt aactaatcac ccctgatata tttttatttt tatatatcca   9060
gttttcattt ttttacgtct tgcctataag ctaatatcat aaataaggtt gtttaagacg   9120
tgcttcaaat atccatatta accactattt ttcaaggaag tatggaaaag tacactctgt   9180
```

-continued

```
cactttgtca ctcgatgtca ttccaaagtt attgcctact aagtaatgac tgtcatgaaa   9240
gcagcattga aataatttgt ttaaaggggg cactctttta aacgggaaga aaatttccgc   9300
ttcctggtct tatcatggac aatttgggct ataggcatga aggaagtggg attacctcag   9360
gaagtcacct tttcttgatt ccagaaacat atgggctgat aaacccgggg tgacctcatg   9420
aaatgagttg cagcagatgt ttattttttt cagaacaagt gatgtttgat ggacctatga   9480
atctatttag ggagacacag atggctggga tccctcccct gtacccttct cactgccagg   9540
agaactacgt gtgaaggtat tcaaggcagg gagtatacat tgctgtttcc tgttgggcaa   9600
tgctccttga ccacattttg ggaagagtgg atgttatcat tgagaaaaca atgtgtctgg   9660
aattaatggg gttcttataa agaaggttcc cagaaaagaa tgttcattcc agcttcttca   9720
ggaaacagga acattcaagg aaaaggacaa tcaggatgtc atcagggaaa tgaaaataaa   9780
aaccacaatg agatatcacc ttataccagg tagatggcta ctataaaaaa atgaagtgtc   9840
atcaaggata tagagaaatt ggaacccttc ttcactgctg gagggaatgg aaaatggtgt   9900
agccgttatg aaaaacagta cggaggtttc tcaaaaatta aaaatagaac tgctatatga   9960
tccagcaatc tcacttctgt atatataccc aaaataattg aaatcagaat ttcaagaaaa  10020
tatttacact cccatgttca ttgtggcact cttcacaatc actgtttcca aagttatgga  10080
aacaacccaa atttccattg gaaaataaat ggacaaagga aatgtgcata taacgtacaa  10140
tggggatatt attcagccta aaaaaagggg ggatcctgtt atttatgaca acatgaataa  10200
acccggaggc cattatgcta tgtaaaatga gcaagtaaca gaaagacaaa tactgcctga  10260
tttcatttat atgaggttct aaaatagtca aactcataga agcagagaat agaacagtgg  10320
ttcctaggga aaaggaggaa gggagaaatg aggaaatagg gagttgtcta attggtataa  10380
aattatagta tgcaagatga attagctcta aagatcagct gtatagcaga gttcgtataa  10440
tgaacaatac tgtattatgc acttaacatt ttgttaagag ggtacctctc atgttaagtg  10500
ttcttaccat atacatatac acaaggaagc ttttggaggt gatggatata tttattacct  10560
tgattgtggt gatggtttga caggtatgtg actatgtcta aactcatcaa attgtataca  10620
ttaaatatat gcagttttat aatatcaaaa aaaaaaaaaa aaaaa                   10665
```

<210> SEQ ID NO 63
<211> LENGTH: 28
<212> TYPE: DNA
<213> ORGANISM: Homo sapiens

<400> SEQUENCE: 63

```
attttgtttt gtttttaaag acttggcc                                         28
```

<210> SEQ ID NO 64
<211> LENGTH: 28
<212> TYPE: DNA
<213> ORGANISM: Homo sapiens

<400> SEQUENCE: 64

```
gtcatgtgta atcattgcag gtggttcc                                         28
```

<210> SEQ ID NO 65
<211> LENGTH: 28
<212> TYPE: DNA
<213> ORGANISM: Homo sapiens

<400> SEQUENCE: 65

```
atgtcttttt attcctgtag gtgtgaaa                                         28
```

<210> SEQ ID NO 66
<211> LENGTH: 30
<212> TYPE: DNA
<213> ORGANISM: Artificial Sequence
<220> FEATURE:
<223> OTHER INFORMATION: A primer

<400> SEQUENCE: 66
gattagcata cttagactac tacctccatg 30

<210> SEQ ID NO 67
<211> LENGTH: 27
<212> TYPE: DNA
<213> ORGANISM: Homo sapiens

<400> SEQUENCE: 67
gatcaacttc tgaaaaagca ttcccac 27

<210> SEQ ID NO 68
<211> LENGTH: 31
<212> TYPE: DNA
<213> ORGANISM: Artificial Sequence
<220> FEATURE:
<223> OTHER INFORMATION: A primer

<400> SEQUENCE: 68
ggttgctgtt ctcaaagtga ttttgggaga a 31

<210> SEQ ID NO 69
<211> LENGTH: 30
<212> TYPE: DNA
<213> ORGANISM: Homo sapiens

<400> SEQUENCE: 69
acctgaagac tggagagtga gttaaatgct 30

<210> SEQ ID NO 70
<211> LENGTH: 1360
<212> TYPE: DNA
<213> ORGANISM: Homo sapiens
<220> FEATURE:
<221> NAME/KEY: misc_feature
<222> LOCATION: (1)...(1360)
<223> OTHER INFORMATION: n = A,T,C or G

<400> SEQUENCE: 70
ttccacttct aagagctgcc tagagtagtc aagattatag agacaaaagt agtgcataga 60
ttcaagggcc tagggaaagg ggaaatgggg agttatttat taatgaatag tggtgatgat 120
tgtacaaaaa tatgaacata attaatgcca ctaaattgtn cacatacaaa tggtcaagat 180
aataaatttt atgttatgtc atgttatgtt atgtgatttt accataatac agaaaatgaa 240
aaaagaaaag aaagaaagta aagcttagcg gtttncatga cttgnccaat gcctcaaagc 300
catgagtcga cccagctgag atctganctt cagtatattc cattctgaaa tcccagactt 360
ttcccaatct tcttgtactt ttcaaactgt gtttcagttg aggtttattt tcagttttgt 420
atgtgagttt cttcgcaaga agggcgggcc aaattgtgtc ctgcaaaaac ctacatatcg 480
aagtcctaac ccctctacct cagactatga ctgtatatgg agagagagcc ttgaaagagg 540
tatgtaaggt agaatgaggt cattatggtg ggccctaatc caacataact ggtgtcctta 600
taagaagggg agattagaat tcagacacac ttgctgacac cttgagttca gactggaagc 660

-continued

```
ctctagaatt gtgagaaaat gaatgtctgt tgtttaagcc acccagtctg tggtatttcc    720

ttatggcagc cccagcaaac taatacaaat agtgtttcca cagctgaaac aaaattggaa    780

aatcaccgtc atcctagaga gttacaaggg ctattttaat agaacctgat tgttttccta    840

aattcaccaa gcccaggcag aggtcagatg actaattggg ataaaagcca actagcttcc    900

tcttgctgtt tctttagcca ctggtctgca ggcgttttct tcttctaact tcctctcctg    960

tgacaaaaga gataactatt agagaaacaa aagtccagaa tgctaaggtt gccgctttca   1020

cttcctctca ccctttagcc cagaactgct ttgaatacac caattgctgt ggggcggctc   1080

gaggaagaga agacaccagt gcctcagaaa ctgctcggtc agacggtgat agcgagccac   1140

gcattcacag ggccactgct gctcacagaa gcagtgagga tgatgccagg atgatgtctg   1200

cctcgcgcct ggctgggact ctgatcccag ccatggcctt cctctcctgc gtgagaccag   1260

aaagctggga gccctgcgtg gaggtatgtg gctggagtca gctcctctga actttccctc   1320

acttctgccc agaacttctc actgtgtgcc ctggtttgtt                         1360
```

<210> SEQ ID NO 71
<211> LENGTH: 1333
<212> TYPE: DNA
<213> ORGANISM: Homo sapiens

<400> SEQUENCE: 71

```
cgcatcatgg atttgtgtgt catccttgtg caggggccat gctcatcttc tctgtatcct     60

tccaatttta gtatatgtgc tactgcagca agcacgatat tggatatttt attacctaca    120

ttttacatat gataaaatga ggctcactga ggtttttctt ttgttcgttt tattttgttt    180

tgtttttaaa gacttggccc taaaccacac agaagagctg gcatgaaacc cagagctttc    240

agactccgga gcctcagccc ttcaccccga ttccattgct tcttgctaaa tgctgccgtt    300

ttatcacgga ggttagaatg ctgagcacgt agtaggtgct ctttactttc taatctagag    360

taagacaatt tataagcatg aattgagtga atggatggat ggatatatgg atggaaggat    420

ggacagatgg atgaaaggtt gactgaattt tgtgcttgca caaaaagagg cccctctcca    480

ccatctctgg tctaggagag gggagttggg agaccatgca gtaaagatac ttcatgtcat    540

gtgtaatcat tgcaggtggt tcctaatatt acttatcaat gcatggagct gaatttctac    600

aaaatccccg acaacctccc cttctcaacc aagaacctgg acctgagctt taatcccctg    660

aggcatttag gcagctatag cttcttcagt ttcccagaac tgcaggtgct ggatttatcc    720

aggtaatgaa tccactttta catactgcac aaggtgaggt gttcattgtc ctatcatttc    780

attattggac tggaaagctt ggtttgtgga gtctcatctt cattcactta ttcattcata    840

caacagatgt cttattaact atataacctt gagcaagcta cctctattct ccaggtctca    900

gttttctaat ctgtgaagta ggcagttggc tgagacagct tctaagggca attctaattt    960

taggttttct tttaagacag gagagaaaat tagcttaaat tctttcataa gcagctattt   1020

attgactact tgctatatgt tgtacactct gcaagaagac aggcatatat tgatatataa   1080

cacacagccc ctgttgttaa ggaggcatat cttcttgaaa gagttaatac cttaaagtcc   1140

tgggtatggt cctgggtaca tagtatatag tcaacacatt ttaattatga ttttttggat   1200

ctggaaactg atataaagat agcgacatat aacagtaggt gataaattat gtttaaacta   1260

aaggtaacta attgtatttt tcagaagagg ggccttctct gtggtgggta gtcaagaaag   1320

attcatgaac tgc                                                      1333
```

-continued

```
<210> SEQ ID NO 72
<211> LENGTH: 6786
<212> TYPE: DNA
<213> ORGANISM: Homo sapiens
<220> FEATURE:
<221> NAME/KEY: misc_feature
<222> LOCATION: (1)...(6786)
<223> OTHER INFORMATION: n = A,T,C or G

<400> SEQUENCE: 72

ggtaagaatg ctttgtgata gcccagcagc cttctttccc ctatagaaat atatatatan     60
tctttttata ggtgaggaac tgaagcttga ataatttaaa tgacttatat acatnatcat    120
tgcttgttag ccacagacca gagatttaag ttcncatctc cagaatccaa cttaaatgtt    180
ttctttgtct taatactcta cttctctaaa gtgattatca ccaatgtaat gatatagagn    240
cacagcaaga ccctttcctt ctcacctaat gtatagagca atgcagagat agaatgatgg    300
gctataacaa tcatataatt gaaagaaaga acttcaaaaa taatcaagtt cagctgtttg    360
atttataaat gtgataacta aaacctagag aggaaaagag gtactcaaga tcacacagta    420
ggagaggact gcagaaacac caaacccaag ctcttttgtc cactcttcca gcgttctttc    480
tactatactg cctatccttt atctagttac caataaataa caaaagcttg gaccacaatg    540
cttttattgt ctaggaaact cctgaagaag ctaaataaaa tgggtgggga atattgtaaa    600
tgtaattcag gctggattaa gaaagaactt atttgacatt gtaactgaca agcacctgca    660
atgctgaaag gaatttttca ttggcntgct gtttgctggg ctgcatcaaa gccctgtctc    720
taggacatgt ctctgaacat tgtgtgtagc atggctttca tttcttttag gataaaattc    780
aaaacccttt atctggttgg taaacctctg cctaattggg aaccttcttt ctccacaact    840
ccatattgta cactccaatt tcatctctgt tctccaacca tggaagctat ttgtcatgat    900
tcctccttgt gtcatttttt ttctgtcaac cttggggctt ttgtgtttgc tgttcacttc    960
acctcctttt attgttaact tctactcatc tttcaatttt caacttaagt gttctcagag   1020
aaacctactt tgattttctt ggtccanaac ggttctctgg atgtgaactc ttatagcaca   1080
taattttcac ttttttccac aaaactcgct cctatcacct gttacaagca tttacctctg   1140
ataacaagaa ctttcaaata tctagctgtc atgtaagcac ttttcataaa cattaagagt   1200
atctgtgaca cttatgtgta atgtttcgta tctctgaaat tgatatttac cagtcattta   1260
tcttggctac caactaacaa ctatccatat tatctgtacc aatcagatgt ataatcacaa   1320
ttttgtgtga cagaaaatgg ctaaacttga tccaaggcta ttacatgctt tatcaactgc   1380
acaatcttta tatatgtcaa ttattgatct ttanctgatt tccttcttat ggattttctc   1440
ctctgcttat catgtatgcc taacatgaca aaaaagagcc tatcattgca gccagtatga   1500
taatactcag tctgtggggc ttcttatttg cttattccat catcatctgt cctgcttgat   1560
gtctttgcct atgcacaatc atatgaccca tcacatctgt atgaagagct ggatgactag   1620
gattaatatt ctattttagg ttcttattca gcagaaatat tagataatca atgtcttttt   1680
attcctgtag gtgtgaaatc cagacaattg aagatggggc atatcagagc ctaagccacc   1740
tctctacctt aatattgaca ggaaacccca tccagagttt agccctggga gccttttctg   1800
gactatcaag tttacagaag ctggtggctg tggagacaaa tctagcatct ctagagaact   1860
tccccattgg acatctcaaa actttgaaag aacttaatgt ggctcacaat cttatccaat   1920
ctttcaaatt acctgagtat ttttctaatc tgaccaatct agagcacttg gacctttcca   1980
gcaacaagat tcaaagtatt tattgcacag acttgcgggt tctacatcaa atgcccctac   2040
```

-continued

```
tcaatctctc tttagacctg tccctgaacc ctatgaactt tatccaacca ggtgcattta   2100
aagaaattag gcttcataag ctgactttaa gaaataattt tgatagttta aatgtaatga   2160
aaacttgtat tcaaggtctg gctggtttag aagtccatcg tttggttctg ggagaattta   2220
gaaatgaagg aaacttggaa aagtttgaca aatctgctct agagggcctg tgcaatttga   2280
ccattgaaga attccgatta gcatacttag actactacct cgatgatatt attgacttat   2340
ttaattgttt gacaaatgtt tcttcatttt ccctggtgag tgtgactatt gaaagggtaa   2400
aagacttttc ttataatttc ggatggcaac atttagaatt agttaactgt aaatttggac   2460
agtttcccac attgaaactc aaatctctca aaaggcttac tttcacttcc aacaaaggtg   2520
ggaatgcttt ttcagaagtt gatctaccaa gccttgagtt tctagatctc agtagaaatg   2580
gcttgagttt caaaggttgc tgttctcaaa gtgattttgg gacaaccagc ctaaagtatt   2640
tagatctgag cttcaatggt gttattacca tgagttcaaa cttcttgggc ttagaacaac   2700
tagaacatct ggatttccag cattccaatt tgaaacaaat gagtgagttt tcagtattcc   2760
tatcactcag aaacctcatt taccttgaca tttctcatac tcacaccaga gttgctttca   2820
atggcatctt caatggcttg tccagtctcg aagtcttgaa aatggctggc aattctttcc   2880
aggaaaactt ccttccagat atcttcacag agctgagaaa cttgaccttc ctggacctct   2940
ctcagtgtca actggagcag ttgtctccaa cagcatttaa ctcactctcc agtcttcagg   3000
tactaaatat gagccacaac aacttctttt cattggatac gtttccttat aagtgtctga   3060
actccctcca ggttcttgat tacagtctca atcacataat gacttccaaa aaacaggaac   3120
tacagcattt tccaagtagt ctagctttct taaatcttac tcagaatgac tttgcttgta   3180
cttgtgaaca ccagagtttc ctgcaatgga tcaaggacca gaggcagctc ttggtggaag   3240
ttgaacgaat ggaatgtgca acaccttcag ataagcaggg catgcctgtg ctgagtttga   3300
atatcacctg tcagatgaat aagaccatca ttggtgtgtc ggtcctcagt gtgcttgtag   3360
tatctgttgt agcagttctg gtctataagt tctattttca cctgatgctt cttgctggct   3420
gcataaagta tggtagaggt gaaaacatct atgatgcctt tgttatctac tcaagccagg   3480
atgaggactg ggtaaggaat gagctagtaa agaatttaga agaaggggtg cctccatttc   3540
agctctgcct tcactacaga gactttattc ccggtgtggc cattgctgcc aacatcatcc   3600
atgaaggttt ccataaaagc cgaaaggtga ttgttgtggt gtcccagcac ttcatccaga   3660
gccgctggtg tatctttgaa tatgagattg ctcagacctg gcagtttctg agcagtcgtg   3720
ctggtatcat cttcattgtc ctgcagaagg tggagaagac cctgctcagg cagcaggtgg   3780
agctgtaccg ccttctcagc aggaacactt acctggagtg ggaggacagt gtcctggggc   3840
ggcacatctt ctggagacga ctcagaaaag ccctgctgga tggtaaatca tggaatccag   3900
aaggaacagt gggtacagga tgcaattggc aggaagcaac atctatctga agaggaaaaa   3960
taaaaacctc ctgaggcatt tcttgcccag ctgggtccaa cacttgttca gttaataagt   4020
attaaatgct gccacatgtc aggccttatg ctaagggtga gtaattccat ggtgcactag   4080
atatgcaggg ctgctaatct caaggagctt ccagtgcaga gggaataaat gctagactaa   4140
aatacagagt cttccaggtg ggcatttcaa ccaactcagt caaggaaccc atgacaaaga   4200
aagtcatttc aactcttacc tcatcaagtt gaataaagac agagaaaaca gaaagagaca   4260
ttgttctttt cctgagtctt ttgaatggaa attgtattat gttatagcca tcataaaacc   4320
attttggtag ttttgactga actgggtgtt cactttttcc tttttgattg aatacaattt   4380
aaattctact tgatgactgc agtcgtcaag ggctcctga tgcaagatgc cccttccatt   4440
```

```
ttaagtctgt ctccttacag aggttaaagt ctagtggcta attcctaagg aaacctgatt   4500

aacacatgct cacaaccatc ctggtcattc tcgagcatgt tctatttttt aactaatcac   4560

ccctgatata tttttatttt tatatatcca gttttcattt ttttacgtct tgcctataag   4620

ctaatatcat aaataaggtt gtttaagacg tgcttcaaat atccatatta accactattt   4680

ttcaaggaag tatggaaaag tacactctgt cactttgtca ctcgatgtca ttccaaagtt   4740

attgcctact aagtaatgac tgtcatgaaa gcagcattga aataatttgt ttaaaggggg   4800

cactctttta aacgggaaga aaatttccgc ttcctggtct tatcatggac aatttgggct   4860

agaggcagga aggaagtggg atgacctcag gaggtcacct tttcttgatt ccagaaacat   4920

atgggctgat aaacccgggg tgacctcatg aaatgagttg cagcagaagt ttattttttt   4980

cagaacaagt gatgtttgat ggacctctga atctctttag ggagacacag atggctggga   5040

tccctcccct gtacccttct cactgccagg agaactacgt gtgaaggtat tcaaggcagg   5100

gagtatacat tgctgtttcc tgttgggcaa tgctccttga ccacattttg ggaagagtgg   5160

atgttatcat tgagaaaaca atgtgtctgg aattaatggg gttcttataa agaaggttcc   5220

cagaaaagaa tgttcatcca gcctcctcag aaacagaaca ttcaagaaaa ggacaatcag   5280

gatgtcatca gggaaatgaa aataaaaacc acaatgagat atcaccttat accaggtaga   5340

atggctacta taaaaaaatg aagtgtcatc aaggatatag agaaattgga acccttcttc   5400

actgctggag ggaatggaaa atggtgtagc cgttatgaaa aacagtacgg aggtttctca   5460

aaaattaaaa atagaactgc tatatgatcc agcaatctca cttctgtata tatacccaaa   5520

ataattgaaa tcagaatttc aagaaaatat ttacactccc atgttcattg tggcactctt   5580

cacaatcact gtttccaaag ttatggaaac aacccaaatt tccattgaaa aataaatgga   5640

caaagaaaat gtgcatatac gtacaatggg atattattca gcctaaaaaa agggggnatc   5700

ctgttattta tgacaacatg aataaacccg gagccattat gctatgtaaa atgagcaagt   5760

aacagaaaga caaatactgc ctgatttcat ttatatgagg ttctaaaata gtcaaactca   5820

tagaagcaga gaatagaaca gtggttccta gggaaaagga ggaagggaga aatgaggaaa   5880

tagggagttg tctaattggt ataaaattat agtatgcaag atgaattagc tctaaagatc   5940

agctgtatag cagagttcgt ataatgaaca atactgtatt atgcacttaa cattttgtta   6000

agagggtacc tctcatgtta agtgttctta ccatatacat atacacaagg aagcttttgg   6060

aggtgatgga tatatttatt accttgattg tggtgatggt ttgacaggta tgtgactatg   6120

tctaaactca tcaaattgta tacattaaat atatgcagtt ttataatatc aattatgtct   6180

gaatgaagct ataaaaaaga aaagacaaca aaattcagtt gtcaaaactg gaaatatgac   6240

cacagtcaga agtgtttgtt actgagtgtt tcagagtgtg tttggtttga gcaggtctag   6300

ggtgattgaa catccctggg tgtgtttcca tgtctcatgt actagtgaaa gtagatgtgt   6360

gcatttgtgc acatatccct atgtatccct atcagggctg tgtgtatttg aaagtgtgtg   6420

tgtccgcatg atcatatctg tatagaagag agtgtgatta tatttcttga agaatacatc   6480

catttgaaat ggatgtctat ggctgtttga gatgagttct ctactcttgt gcttgtacag   6540

tagtctcccc ttatccctta tgcttggtgg atacgttctt agaccccaag tggatctctg   6600

agaccgcaga tggtaccaaa cctcatatat gcaatatttt ttcctataca taaataccta   6660

agataaagtt catcttctga attaggcaca gtaagagatt aacaataact aacaataaaa   6720
```

-continued

```
ttgaatagtt ataataatat attgtaataa aagttatgtg aatgtgatct ctttcttttc   6780

tctctc                                                              6786
```